(12) United States Patent
Karwoski et al.

(10) Patent No.: US 8,882,678 B2
(45) Date of Patent: Nov. 11, 2014

(54) PLEURAL DRAINAGE SYSTEM AND METHOD OF USE

(75) Inventors: Theodore Karwoski, Hollis, NH (US); James Croteau, Fitchburg, MA (US); Ralph Gillis, Londonderry, NH (US); Joanne Krawczyk, Dunstable, MA (US); Nicholas Want, Manchester, NH (US)

(73) Assignee: Atrium Medical Corporation, Hudson, NH (US)

( * ) Notice: Subject to any disclaimer, the term of this patent is extended or adjusted under 35 U.S.C. 154(b) by 1140 days.

(21) Appl. No.: 12/723,074

(22) Filed: Mar. 12, 2010

(65) Prior Publication Data

US 2011/0071415 A1    Mar. 24, 2011

Related U.S. Application Data

(60) Provisional application No. 61/160,037, filed on Mar. 13, 2009.

(51) Int. Cl.
*A61M 1/00* (2006.01)

(52) U.S. Cl.
CPC ................................. *A61M 1/0023* (2013.01)
USPC ....................................................... 600/541

(58) Field of Classification Search
USPC ........... 600/573, 581; 604/540, 541, 317, 319
See application file for complete search history.

(56) References Cited

U.S. PATENT DOCUMENTS

| | | |
|---|---|---|
| 3,693,613 A | 9/1972 | Kelman |
| 3,902,495 A | 9/1975 | Weiss et al. |
| 3,938,540 A | 2/1976 | Holbrook et al. |
| 3,946,735 A | 3/1976 | DeWall |
| 3,982,546 A | 9/1976 | Friend |
| 4,015,603 A | 4/1977 | Kurtz et al. |
| 4,018,224 A | 4/1977 | Kurtz et al. |
| 4,052,987 A | 10/1977 | Wuchinich et al. |
| 4,073,294 A | 2/1978 | Stanley et al. |

(Continued)

FOREIGN PATENT DOCUMENTS

| | | |
|---|---|---|
| EP | 2080530 A1 | 7/2009 |
| WO | WO0026537 A1 | 5/2000 |

(Continued)

OTHER PUBLICATIONS

International Search Report for Application No. PCT/US11/22985 dated Jul. 20, 2011.

*Primary Examiner* — Sean Dougherty
*Assistant Examiner* — Michael C Stout
(74) *Attorney, Agent, or Firm* — RatnerPrestia

(57) ABSTRACT

A pleural drainage system having an inflatable membrane and a method of using the system are disclosed. The pleural drainage system includes a pleural drainage catheter system. The pleural drainage catheter system includes an inflatable membrane and a drainage catheter integrally coupled to the inflation membrane, the drainage catheter defining a drainage lumen through which fluid is drawn from the pleural cavity, and an inflation lumen coupled for flow of inflation fluid to and from an interior of the inflatable membrane. The pleural drainage system further includes a suction system coupled to the drainage catheter and a fluid collector coupled to receive fluid from the drainage catheter. The pleural drainage system further includes an inflation system connected to deliver inflation fluid to the interior of the inflatable membrane. The pleural drainage system may be used to monitor an associated airleak in the pleural cavity of a patient.

15 Claims, 23 Drawing Sheets

(56) References Cited

U.S. PATENT DOCUMENTS

| | | | |
|---|---|---|---|
| 4,112,948 A | 9/1978 | Kurtz et al. | |
| 4,233,983 A * | 11/1980 | Rocco | 604/97.01 |
| 4,287,889 A | 9/1981 | Stupar | |
| 4,296,748 A | 10/1981 | Kurtz et al. | |
| 4,324,262 A * | 4/1982 | Hall | 600/569 |
| 4,327,720 A * | 5/1982 | Bronson et al. | 128/207.15 |
| 4,372,336 A | 2/1983 | Cornell et al. | |
| 4,396,386 A | 8/1983 | Kurtz et al. | |
| 4,405,309 A | 9/1983 | Kurtz et al. | |
| 4,425,125 A | 1/1984 | Kurtz et al. | |
| 4,439,189 A | 3/1984 | Sargeant et al. | |
| 4,439,190 A | 3/1984 | Protzmann et al. | |
| 4,455,141 A | 6/1984 | Todd | |
| 4,468,226 A | 8/1984 | Kurtz et al. | |
| 4,469,484 A | 9/1984 | Kurtz et al. | |
| 4,475,904 A | 10/1984 | Wang | |
| 4,519,796 A | 5/1985 | Russo | |
| 4,542,643 A | 9/1985 | Himmelstein | |
| 4,563,171 A | 1/1986 | Bodicky | |
| 4,569,674 A | 2/1986 | Phillips et al. | |
| 4,578,060 A | 3/1986 | Huck et al. | |
| 4,605,400 A | 8/1986 | Kurtz et al. | |
| 4,619,647 A | 10/1986 | Kurtz et al. | |
| 4,643,197 A | 2/1987 | Greene et al. | |
| 4,650,476 A | 3/1987 | Telang | |
| 4,650,477 A | 3/1987 | Johnson | |
| 4,654,029 A | 3/1987 | D'Antonio | |
| 4,655,745 A * | 4/1987 | Corbett | 604/540 |
| 4,675,010 A | 6/1987 | Siposs et al. | |
| 4,675,011 A | 6/1987 | Kurtz et al. | |
| 4,715,855 A | 12/1987 | D'Antonio et al. | |
| 4,735,606 A | 4/1988 | Davison | |
| 4,740,202 A | 4/1988 | Stacey et al. | |
| 4,747,843 A | 5/1988 | Felix et al. | |
| 4,747,844 A | 5/1988 | Elliott | |
| 4,767,417 A | 8/1988 | Boehringer et al. | |
| 4,781,678 A | 11/1988 | de Couet et al. | |
| 4,784,642 A | 11/1988 | Everett, Jr. et al. | |
| 4,822,346 A | 4/1989 | Elliott | |
| 4,826,494 A | 5/1989 | Richmond et al. | |
| 4,828,552 A | 5/1989 | Malette | |
| 4,832,685 A | 5/1989 | Haines | |
| 4,883,476 A | 11/1989 | Kurtz et al. | |
| 4,889,531 A | 12/1989 | D'Antonio et al. | |
| 4,894,056 A | 1/1990 | Bommarito | |
| 4,902,284 A | 2/1990 | D'Antonio et al. | |
| 4,911,697 A | 3/1990 | Kerwin | |
| 4,923,451 A | 5/1990 | McCormick | |
| 4,929,244 A | 5/1990 | Swisher | |
| 4,955,874 A | 9/1990 | Farrar et al. | |
| 4,963,135 A | 10/1990 | Kerwin | |
| 4,990,137 A | 2/1991 | Graham | |
| 4,994,050 A | 2/1991 | Weilbacher et al. | |
| 5,019,060 A | 5/1991 | Goosen | |
| 5,026,358 A | 6/1991 | Everett, Jr. et al. | |
| 5,037,407 A | 8/1991 | Kurtz | |
| 5,141,503 A | 8/1992 | Sewell, Jr. | |
| 5,158,533 A | 10/1992 | Strauss et al. | |
| 5,286,262 A | 2/1994 | Herweck et al. | |
| 5,300,050 A | 4/1994 | Everett, Jr. et al. | |
| 5,370,610 A | 12/1994 | Reynolds | |
| 5,380,314 A | 1/1995 | Herweck et al. | |
| 5,397,299 A | 3/1995 | Karwoski et al. | |
| 5,507,734 A | 4/1996 | Everett, Jr. et al. | |
| 5,520,652 A | 5/1996 | Peterson | |
| 5,643,229 A | 7/1997 | Sinaiko | |
| 5,738,656 A | 4/1998 | Wagner | |
| 5,800,393 A * | 9/1998 | Sahota | 604/103.07 |
| 5,807,358 A | 9/1998 | Herweck et al. | |
| 5,897,534 A | 4/1999 | Heim et al. | |
| 5,931,821 A | 8/1999 | Weilbacher et al. | |
| 5,944,703 A | 8/1999 | Dixon et al. | |
| 5,971,956 A | 10/1999 | Epstein | |
| 5,989,234 A | 11/1999 | Valerio et al. | |
| 6,007,521 A * | 12/1999 | Bidwell et al. | 604/264 |
| 6,017,493 A | 1/2000 | Cambron et al. | |
| 6,024,731 A | 2/2000 | Seddon et al. | |
| 6,099,493 A | 8/2000 | Swisher | |
| 6,123,697 A * | 9/2000 | Shippert | 604/514 |
| 6,142,982 A | 11/2000 | Hunt et al. | |
| 6,254,591 B1 * | 7/2001 | Roberson | 604/541 |
| 6,283,719 B1 | 9/2001 | Frantz et al. | |
| 6,299,593 B1 | 10/2001 | Wakabayashi | |
| 6,338,728 B1 | 1/2002 | Valerio et al. | |
| 6,352,525 B1 | 3/2002 | Wakabayashi | |
| 6,371,124 B1 | 4/2002 | Whelan | |
| 6,371,947 B1 | 4/2002 | Gibertoni | |
| 6,447,491 B1 | 9/2002 | Lord | |
| 6,514,232 B1 | 2/2003 | Gibertoni | |
| 6,537,495 B1 | 3/2003 | Cambron et al. | |
| 6,558,341 B1 | 5/2003 | Swisher | |
| 6,592,602 B1 | 7/2003 | Peartree et al. | |
| 6,626,877 B2 | 9/2003 | Hand et al. | |
| 6,749,592 B2 | 6/2004 | Lord | |
| 6,837,868 B1 * | 1/2005 | Fajnsztajn | 604/96.01 |
| 6,849,061 B2 * | 2/2005 | Wagner | 604/99.02 |
| 6,881,204 B1 | 4/2005 | Bunce | |
| 6,902,550 B2 | 6/2005 | Want et al. | |
| 6,955,664 B2 | 10/2005 | D'Antonio | |
| 6,976,977 B2 | 12/2005 | Yam | |
| D517,897 S | 3/2006 | Want et al. | |
| 7,207,946 B2 | 4/2007 | Sirokman | |
| 7,232,105 B2 | 6/2007 | Want et al. | |
| 7,264,616 B2 | 9/2007 | Shehada et al. | |
| 7,326,197 B2 * | 2/2008 | Breznock et al. | 604/541 |
| 7,419,483 B2 * | 9/2008 | Shehada | 604/543 |
| 7,674,248 B2 | 3/2010 | Anderson et al. | |
| 7,695,467 B2 * | 4/2010 | Breznock et al. | 604/541 |
| 8,070,736 B2 * | 12/2011 | Nishtala et al. | 604/328 |
| 8,075,539 B2 * | 12/2011 | Nishtala et al. | 604/328 |
| 8,152,786 B2 * | 4/2012 | Shapland et al. | 604/321 |
| 8,252,003 B2 * | 8/2012 | Tanaka et al. | 606/108 |
| 8,267,917 B2 * | 9/2012 | Jabbour et al. | 604/540 |
| 2001/0056273 A1 * | 12/2001 | Ewers | 604/509 |
| 2002/0058915 A1 | 5/2002 | Wakabayashi | |
| 2002/0082568 A1 | 6/2002 | Yam | |
| 2002/0193761 A1 | 12/2002 | Lord | |
| 2002/0198505 A1 | 12/2002 | Want et al. | |
| 2003/0028175 A1 | 2/2003 | D'Antonio | |
| 2003/0100890 A1 * | 5/2003 | Waddell et al. | 604/541 |
| 2004/0040560 A1 * | 3/2004 | Euliano et al. | 128/204.23 |
| 2004/0059303 A1 | 3/2004 | Anderson et al. | |
| 2004/0078026 A1 * | 4/2004 | Wagner | 604/541 |
| 2004/0106874 A1 * | 6/2004 | Eigler et al. | 600/486 |
| 2004/0143227 A1 | 7/2004 | Rollin et al. | |
| 2004/0143228 A1 | 7/2004 | Anderson et al. | |
| 2004/0204693 A1 | 10/2004 | Anderson et al. | |
| 2004/0230179 A1 * | 11/2004 | Shehada | 604/541 |
| 2004/0260255 A1 | 12/2004 | Charlez | |
| 2004/0267215 A1 | 12/2004 | Charlez | |
| 2005/0016287 A1 | 1/2005 | Corbeil et al. | |
| 2005/0054994 A1 * | 3/2005 | Cioanta et al. | 604/317 |
| 2005/0137539 A1 | 6/2005 | Biggie et al. | |
| 2005/0154359 A1 * | 7/2005 | Charlez | 604/317 |
| 2005/0154373 A1 | 7/2005 | Deutsch | |
| 2005/0192548 A1 | 9/2005 | Dolliver et al. | |
| 2006/0036221 A1 | 2/2006 | Watson, Jr. | |
| 2006/0122575 A1 | 6/2006 | Wakabayashi | |
| 2006/0149170 A1 | 7/2006 | Boynton et al. | |
| 2006/0149599 A1 * | 7/2006 | Fox et al. | 705/3 |
| 2006/0206097 A1 * | 9/2006 | Breznock et al. | 604/541 |
| 2007/0010798 A1 | 1/2007 | Stoller et al. | |
| 2007/0038170 A1 * | 2/2007 | Joseph et al. | 604/6.16 |
| 2007/0056264 A1 * | 3/2007 | Hou et al. | 60/274 |
| 2007/0078444 A1 | 4/2007 | Larsson | |
| 2007/0100324 A1 * | 5/2007 | Tempel et al. | 604/541 |
| 2007/0142742 A1 * | 6/2007 | Aljuri et al. | 600/538 |
| 2007/0219488 A1 | 9/2007 | Francescatti | |
| 2007/0219532 A1 | 9/2007 | Karpowicz | |
| 2007/0219534 A1 | 9/2007 | Phung et al. | |
| 2007/0219537 A1 * | 9/2007 | Phung et al. | 604/541 |
| 2008/0033028 A1 * | 2/2008 | Berthelette et al. | 514/411 |
| 2008/0103523 A1 * | 5/2008 | Chiu et al. | 606/200 |
| 2008/0114300 A1 | 5/2008 | Muri et al. | |

(56) References Cited

U.S. PATENT DOCUMENTS

| | | |
|---|---|---|
| 2008/0119802 A1 | 5/2008 | Riesinger |
| 2008/0183156 A1 | 7/2008 | Yoo |
| 2008/0269582 A1 | 10/2008 | Mansour et al. |
| 2009/0030383 A1 | 1/2009 | Larsen et al. |
| 2009/0157019 A1 | 6/2009 | Koch et al. |
| 2009/0163853 A1 | 6/2009 | Cull et al. |
| 2009/0163863 A1 | 6/2009 | Lutwyche |
| 2009/0188531 A1 | 7/2009 | Boyle, Jr. |
| 2009/0198201 A1 | 8/2009 | Adahan |
| 2009/0235935 A1* | 9/2009 | Pacey ........................ 128/207.14 |
| 2009/0264833 A1 | 10/2009 | Boyle, Jr. |
| 2009/0264837 A1 | 10/2009 | Adahan |
| 2009/0266146 A1 | 10/2009 | Fontanili et al. |
| 2009/0281523 A1* | 11/2009 | Sacco et al. ................... 604/523 |
| 2010/0222754 A1* | 9/2010 | Nishtala et al. ............... 604/328 |
| 2011/0060300 A1 | 3/2011 | Weig et al. |
| 2011/0190737 A1* | 8/2011 | Rocco .......................... 604/544 |

FOREIGN PATENT DOCUMENTS

| | | |
|---|---|---|
| WO | WO2004/110523 A1 | 12/2004 |
| WO | WO2007024230 A1 | 3/2007 |
| WO | WO2009005424 A1 | 1/2009 |
| WO | WO2009120400 A3 | 2/2010 |
| WO | WO2010021775 A1 | 2/2010 |
| WO | WO2010026458 A1 | 3/2010 |

* cited by examiner

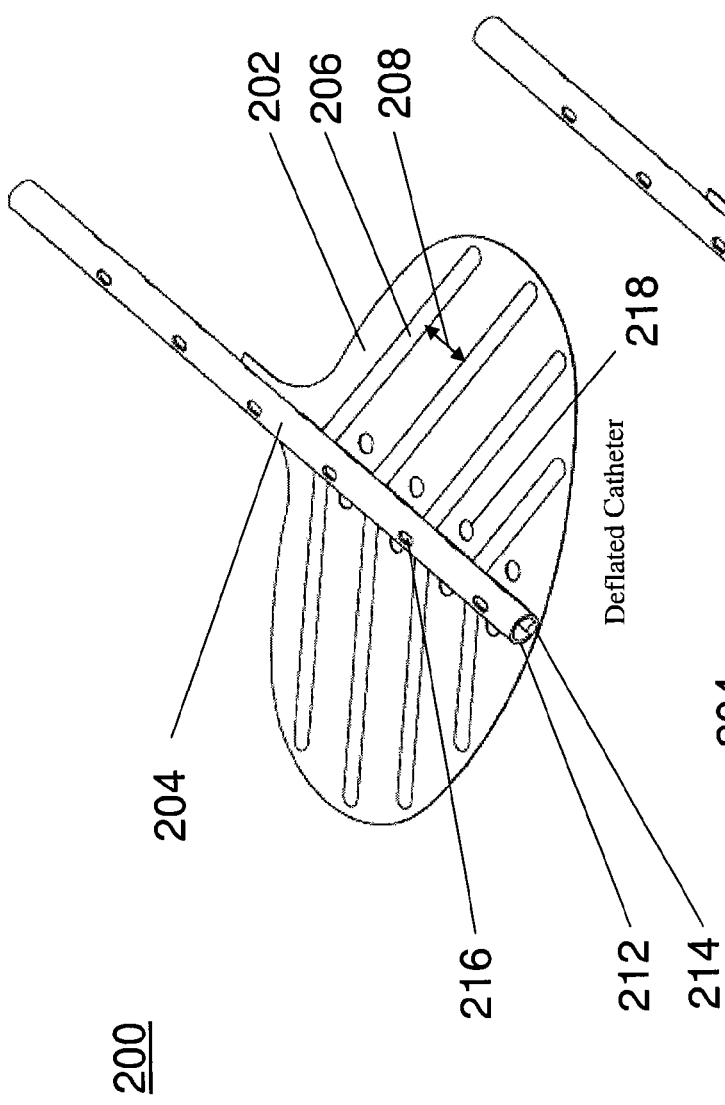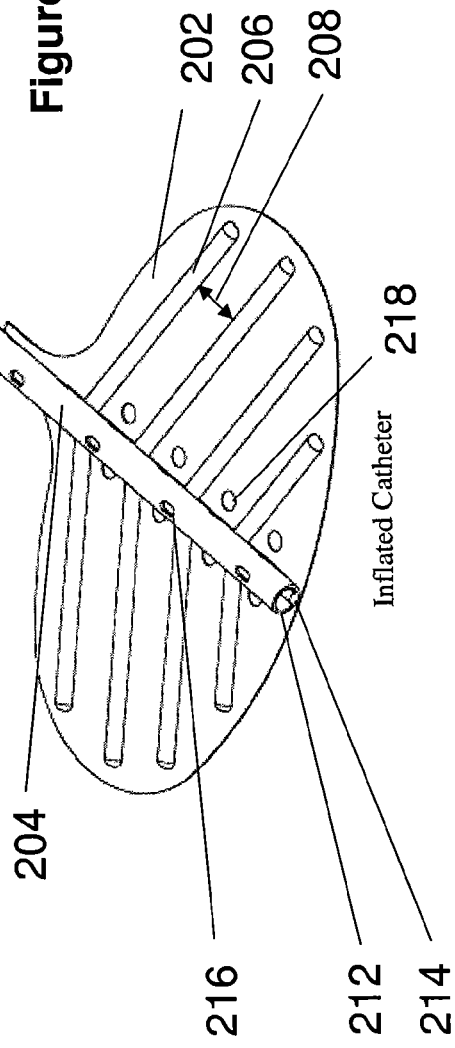

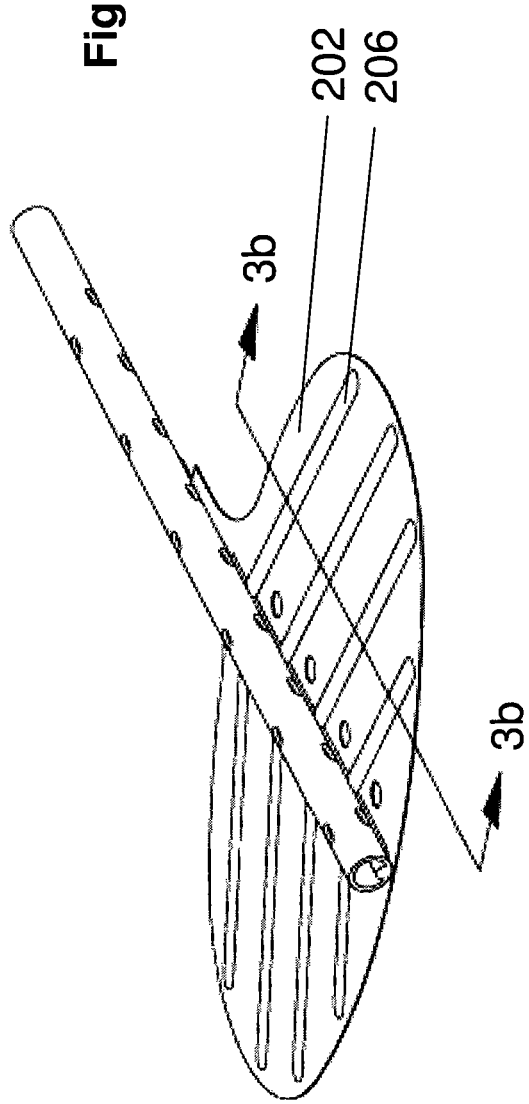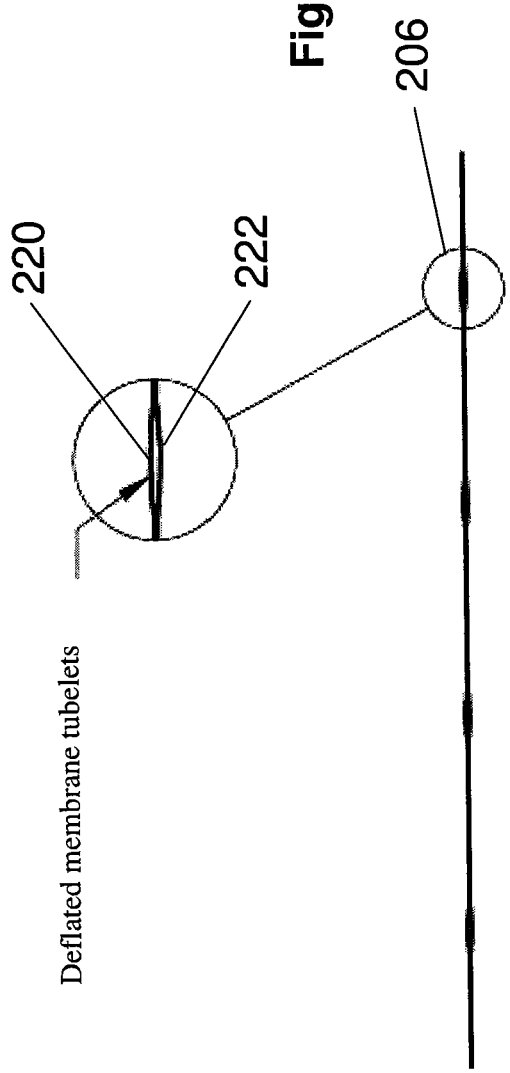

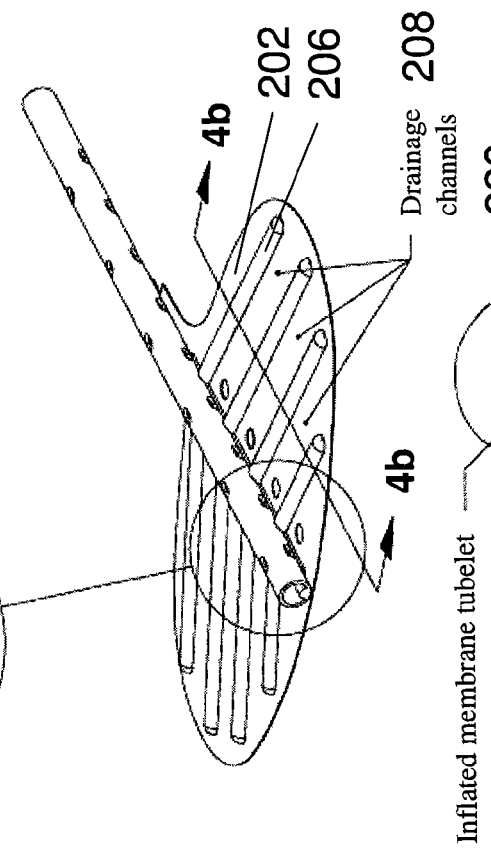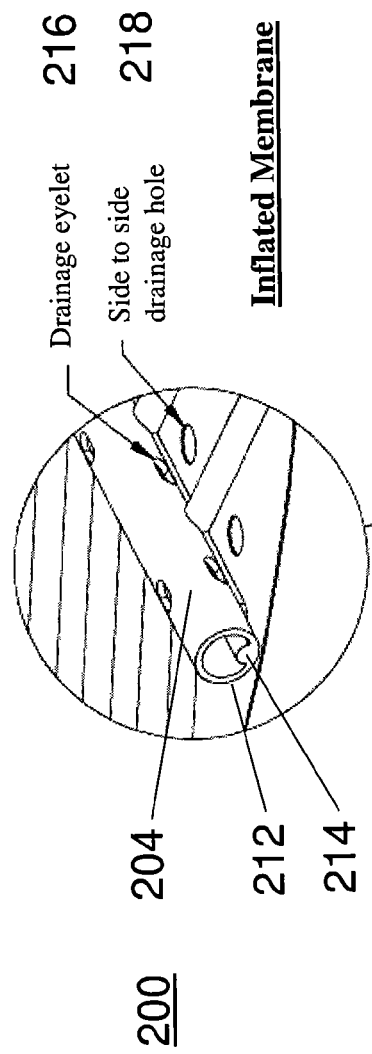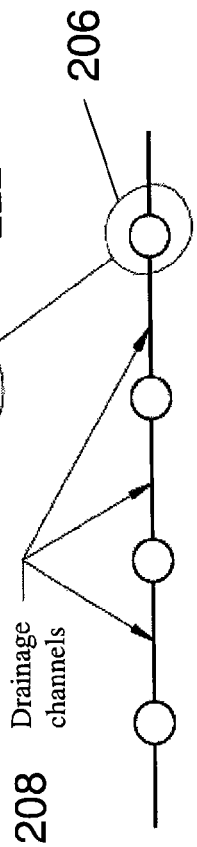
Figure 4a
Figure 4b

A number of fluid recovery systems have been developed for withdrawing fluid, such as air and/or blood, from a patient after chest surgery or trauma. Such systems are intended to remove fluid from the pleural space or the mediastinal cavity and to restore the sub-atmospheric pressure that is normally present in the pleural space. The systems are usually adapted to allow suction to be applied to the chest cavity to facilitate, among other things, the removal of fluid from the pleural space. Once the fluid has been removed, the pleural cavity is allowed to heal and the normal condition of the pleural space is restored.

PLEURAL DRAINAGE SYSTEM AND METHOD OF USE

CROSS REFERENCE TO RELATED APPLICATIONS

This application claims the benefit of U.S. Provisional Patent Application No. 61/160,037, filed Mar. 13, 2009, the contents of which are incorporated herein by reference in their entirety.

FIELD OF THE INVENTION

The field of the invention relates to thoracic systems, and more particularly to pleural drainage systems.

BACKGROUND OF THE INVENTION

Despite many developments in the field of pleural drainage, there remains a need for improved pleural drainage systems. Specifically, there remains a need for pleural drainage systems that can provide one or more of improved drainage of fluid from the pleural cavity of a patient, monitoring of an airleak in a pleural cavity of a patient, and/or the delivery of a therapeutic treatment to the pleural cavity of a patient.

SUMMARY OF THE INVENTION

According to one aspect of the present invention, a pleural drainage catheter system is provided. The pleural drainage catheter system is configured to extend into a pleural cavity of a patient and to drain fluid from the pleural cavity of the patient. The pleural drainage catheter system includes an inflatable membrane comprising two opposed layers formed from a bio-compatible material, the inflatable membrane having a deflated state in which the layers are positioned substantially adjacent one another and an inflated state in which at least portions of the respective layers are spaced from one another. An external surface of the inflatable membrane defines one or more passages that facilitate the movement of fluid along the external surface for removal from the pleural cavity. The pleural drainage catheter system further includes a drainage catheter integrally coupled to the inflation membrane, the drainage catheter defining a drainage lumen, a plurality of drainage openings through which fluid is drawn into the drainage lumen from the pleural cavity, and an inflation lumen coupled for flow of inflation fluid to and from an interior of the inflatable membrane.

According to another aspect of the present invention, a method for monitoring an airleak in a pleural cavity of a patient is provided. An airleak in a pleural cavity of a patient may be monitored by measuring a rate of pressure decay in the pleural cavity of the patient. The rate of pressure decay is correlated to an associated airleak of the pleural cavity of the patient according to the following formula: $Q_{Airleak} \alpha \int P dt$, where $Q_{Airleak}$ is an extrapolated airleak, P is a measured pressure, and t is time. An indicator is generated showing a trend in the magnitude of the airleak of the pleural cavity.

According to yet another aspect of the present invention, a pleural drainage system is provided. The pleural drainage system is configured to deliver a therapeutic treatment to the pleural cavity of a patient. The pleural drainage system includes a pleural drainage catheter system including an inflatable membrane having a deflated state and an inflated state. The pleural drainage catheter system also includes a drainage catheter coupled to the inflation membrane, the drainage catheter defining a drainage lumen, a plurality of drainage openings through which fluid is drawn into the drainage lumen from the pleural cavity, and an inflation lumen coupled for flow of inflation fluid to and from an interior of the inflatable membrane. The pleural drainage system further includes a suction system coupled to the drainage catheter of the pleural drainage catheter system and connected to apply suction to the drainage lumen of the drainage catheter and to draw fluid into the drainage lumen of the drainage catheter through the drainage openings defined by the drainage catheter. The pleural drainage system further includes a fluid collector coupled to receive fluid from the drainage lumen of the drainage catheter. The pleural drainage system further includes an inflation system coupled to the drainage catheter of the pleural drainage catheter system and connected to apply pressure to the inflation lumen of the drainage catheter and to deliver inflation fluid to the interior of the inflatable membrane through the inflation lumen defined by the drainage catheter.

According to still another aspect of the present invention, a pleural drainage system includes a drainage catheter, a suction system, a fluid collector, a pressure sensor, a processor, and a plurality of indicators. The drainage catheter defines a drainage lumen and at least one drainage opening through which fluid is drawn into the drainage lumen from a pleural cavity. The suction system is coupled to apply suction to the drainage lumen in order to draw fluid into the drainage lumen through the at least one drainage opening. The fluid collector is coupled to receive fluid from the drainage lumen of the drainage catheter. The pressure sensor is coupled to the suction system and is positioned to sense a pressure in the pleural cavity. The processor is coupled to receive a signal from the pressure sensor based on the sensed pressure in the pleural cavity. The indicators are coupled to the processor and configured to visually indicate a status corresponding to the sensed pressure in the pleural cavity to an operator. The processor is configured to selectively activate the plurality of indicators such that a first indicator of the plurality of indicators is activated when the sensed pressure is within a first predefined range, a second indicator of the plurality of indicator is activated when the sensed pressure is within a second predefined range, and a third indicator of the plurality of indicators is activated when the sensed pressure is within a third predefined range.

According to another aspect of the present invention, a pleural drainage system includes a drainage catheter, a suction system, and a fluid collector. The drainage catheter defines a drainage lumen and at least one drainage opening through which fluid is drawn into the drainage lumen from a pleural cavity. The suction system is coupled to apply suction to the drainage lumen in order to draw fluid into the drainage lumen through the at least one drainage opening. The suction system includes a pump, an accumulator in fluid communication with the pump, and a valve coupled between the accumulator and the drainage catheter. The fluid collector is coupled to receive fluid from the drainage lumen of the drainage catheter. The pump is configured to generate a negative pressure in the accumulator. The valve is configured to open when there is a blockage between the pleural cavity and the fluid collector. The opening of the valve causes the negative pressure in the accumulator to be applied to the drainage catheter such that the blockage is drawn into the fluid collector.

BRIEF DESCRIPTION OF THE DRAWINGS

The invention is best understood from the following detailed description when read in connection with the accompanying drawings. It is emphasized that, according to common practice, the various features of the drawings are not to scale. On the contrary, the dimensions of the various features are arbitrarily expanded or reduced for clarity. Included in the drawings are the following figures:

FIGS. 2a and 2b are perspective views of another exemplary embodiment of a pleural drainage catheter system according to an aspect of the present invention;

FIGS. 3a and 3b are perspective and cross-sectional side views of the pleural drainage catheter system shown in FIG. 2a;

FIGS. 4a and 4b are perspective and cross-sectional side views of the pleural drainage catheter system shown in FIG. 2b, in an inflated state;

DETAILED DESCRIPTION OF THE INVENTION

Figure 1:
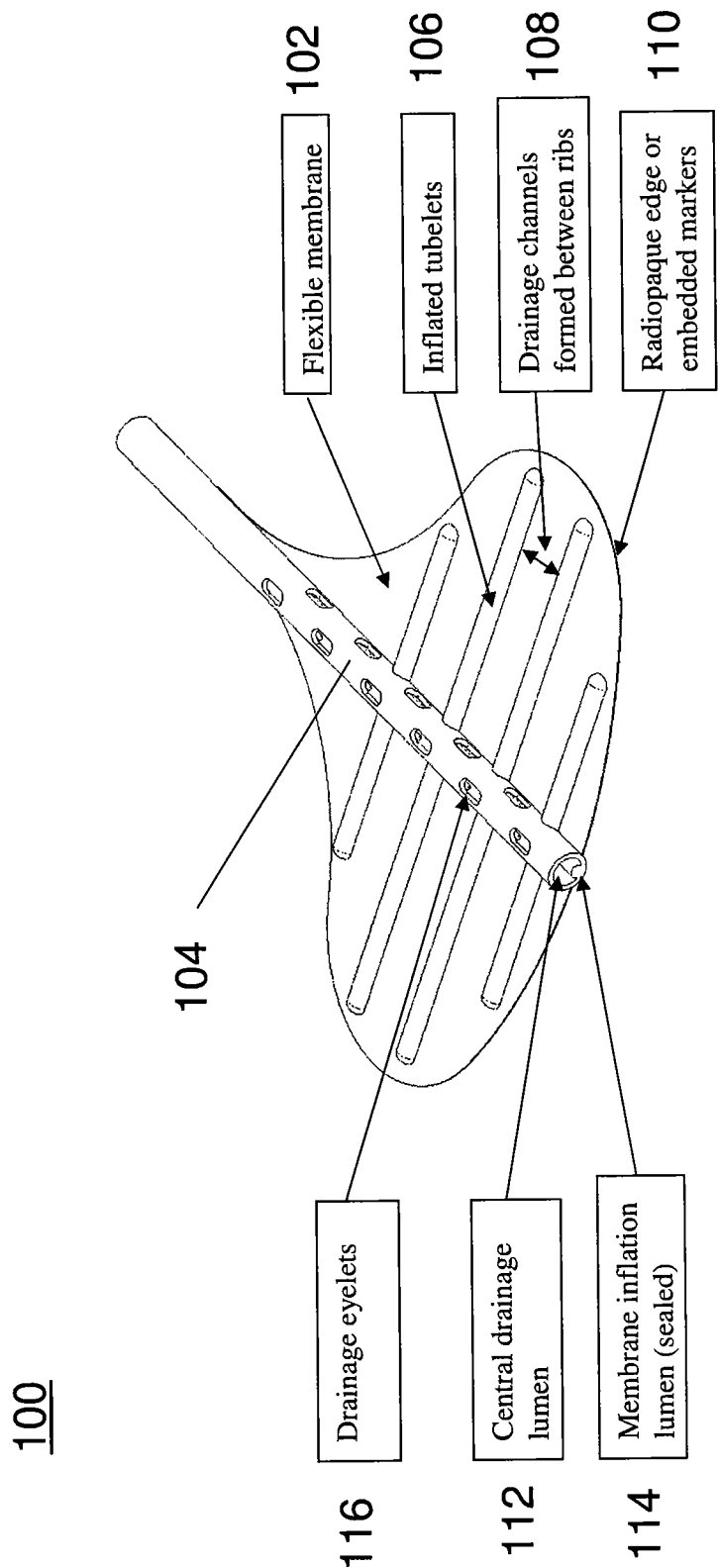
FIG. 1 is a perspective view of an exemplary embodiment of a pleural drainage catheter system according to an aspect of the present invention.

This invention will now be described with reference to several embodiments selected for illustration in the drawings. It will be appreciated that the scope and spirit of the invention are not limited to the illustrated embodiments. It will further be appreciated that the drawings are not rendered to any particular proportion or scale. Also, any dimensions referred to in the description of the illustrated embodiments are provided merely for the purpose of illustration. The invention is not limited to any particular dimensions, materials, or other details of the illustrated embodiments.

FIG. 1 depicts an exemplary embodiment of a pleural drainage catheter system 100 in accordance with an aspect of the present invention. The pleural drainage catheter system 100 is configured to extend into a pleural cavity of a patient (not shown). The pleural drainage catheter system 100 includes an inflatable membrane 102 and a drainage catheter 104 integrally coupled to inflatable membrane 102. The drainage catheter 104 may be centrally located and at least partially surrounded by inflatable membrane 102. Inflatable membrane 102 may further be sealable to enclose drainage catheter 104.

Inflatable membrane 102 is formed from two opposed layers, the two opposed layers optimally being two thin layers of a bio-compatible material. The bio-compatible material may be, for example, polyurethane, polyester, polyethylene elastomers, mylar, PVC, or other polymeric materials.

Inflatable membrane 102 defines one or more tubelets 106 when in an inflated state, the embodiment shown including four such tubelets 106 extending outwardly from each side of drainage catheter 104, though fewer or more such tubelets can be provided. The tubelets 106 may be provided in the form of substantially straight structures, as illustrated, or in other curved or angled shapes to form inflatable ribs. While tubelets 106 are illustrated as primarily straight and cylindrical in shape in this embodiment, it will be understood that tubelets 106 may have other shapes and configurations, as desired. Tubelets 106 may be formed by selectively sealing the two opposed layers of inflatable membrane 102 to define the one or more tubelets 106.

Tubelets 106 may extend in a direction angled with respect to an axis of drainage catheter 104. Specifically, tubelets 106 may extend in a direction substantially perpendicular to an axis of drainage catheter 104 as illustrated. Inflatable membrane 102 can be inserted into a pleural cavity in a deflated or optimally collapsed configuration. This allows for the system 100 to be inserted though significantly smaller openings in the body or through smaller trocar systems than other larger and bulkier tubular devices, thereby reducing tissue trauma and associated pain and discomfort in recovery. System 100 may also be configured for insertion using standard chest tube insertion techniques, as would be known to one of ordinary skill in the art.

Inflatable membrane 102 has a deflated state, in which the inflatable membrane 102 and the one or more tubelets 106 are deflated. In this state, the two opposed layers are positioned substantially adjacent one another. Inflatable membrane 102 also has an inflated state, in which tubelets 106 are inflated. In this state, portions of the respective opposed layers forming tubelets 106 are spaced apart from one another. As will be described later in greater detail, inflation fluid such as an inflation gas or liquid is delivered between the layers of the membrane 102 to inflate the tubelets 106 and, in turn, to inflate portions of the membrane 102. Though inflatable membrane 102 is illustrated with tubelets 106, other shapes or areas of inflatable membrane 102, or the entire inflatable membrane 102, may receive the inflation fluid to inflate membrane 102.

The external surface of inflatable membrane 102 which forms tubelets 106 also defines one or more passages 108 between the tubelets 106. The passages 108 may function as drainage channels such that when inflatable membrane 102 is in the inflated state, passages 108 facilitate the movement of fluid along the external surface of inflatable membrane 102 to drainage catheter 104 for removal from the pleural cavity. As will be described later in greater detail, the inflation of the tubelets 106 will function to separate tissue in the pleural cavity and to separate tissue from the membrane 102 in locations adjacent and/or between the tubelets 106. In that way, gaps or passages or channels are formed that facilitate flow of fluid along or adjacent to surfaces of the membrane 102.

Passages 108 or other structures of the membrane 102 optionally define a drainage opening between tubelets 106 for the flow of fluid from a perimeter portion of inflatable membrane 102, or within the perimeter, to drainage catheter 104.

Inflatable membrane 102 may also include radiopaque edges or markers 110 along the edges of inflatable membrane 102. The radiopaque markers 110 may be positioned to facilitate visualization of inflatable membrane 102 during and after its insertion into the pleural cavity of a patient. According to one exemplary embodiment, one or more markers are positioned along the perimeter of the membrane 102. They can be positioned intermittently at even or varied spacings or a single continuous marker can circumscribe the entire perimeter. Also, markers can be positioned at other locations on or along the membrane 102 or drainage catheter 104 to facilitate visualization. Radiopaque markers 110 may include radiopaque alloys such as, for example, gold, platinum, iridium, palladium, rhodium, or a combination of such alloys. Radiopaque markers 110 may further include radiopacifier materials such as, for example, barium sulfate, bismuth, and tungsten.

Further, inflatable membrane 102 may include a protective coating (not shown) on the external surface of inflatable membrane 102. The protective coating may be configured to resist adhesion or provide therapy to tissue in the pleural cavity of a patient. Examples of adhesion-resistant and/or therapeutic coatings and/or therapeutics include, for example, fish oil, omega 3 fatty acids, antiproliferatives, antineoplastics, paclitaxel, rapamyacin, hyaluronic acid, human plasma-derived surgical sealants, and agents comprised of hyaluronate and carboxymethylcellulose that are combined with dimethylaminopropyl, ethylcarbodimide, hydrochloride, polylactic acid, or PLGA.

Drainage catheter 104 may optionally be a flexible polymer drainage catheter. Suitable materials for drainage catheter 104 include, for example, PVC, low density polyurethane, PTFE, and silicone.

Drainage catheter 104 defines a central drainage lumen 112 and a membrane inflation lumen 114. Central drainage lumen 112 has an open distal end, thus facilitating the suction of fluid located near that end. Drainage catheter 104 also includes a plurality of drainage openings 116 through which fluid is drawn into central drainage lumen 112 and thereby removed from the pleural cavity. The plurality of drainage openings 116 may be drainage eyelets.

The distal end of membrane inflation lumen 114 is preferably closed, as illustrated in FIG. 1, so that inflation fluid can be maintained under controlled pressure for delivery to and removal from the inflatable membrane 102. Membrane inflation lumen 114 is coupled for flow of inflation fluid to and from an interior of inflatable membrane 102. Membrane inflation lumen 114 is specifically coupled for flow of inflation fluid to and from inflatable tubelets 106. Membrane inflation lumen 114 may be formed integrally with a wall of central drainage lumen 112 of drainage catheter 104.

Pleural drainage catheter system 100 is depicted having a tubular drainage catheter 104 and a rounded inflatable membrane 102 when inflated. However, other embodiments including differing configurations and non-tubular shapes for drainage catheter 104 are contemplated. For example, the pleural drainage catheter system 100 may have any number of shapes that can create space to facilitate and optimize fluid drainage, accommodation of organ shift due to lung lobectomies or enhancement of other treatment options such as performing thoracoscopic procedures. Multiple and integrally connected channels or an integrated circular hoop catheter, all being enclosed by or formed in the inflatable membrane 102, may be provided.

Additionally, as will be described later in greater detail, the construction of inflatable membrane 102 may be such that the two opposing layers forming membrane 102 are made of materials or thickness to provide a preferential curve or bias of the membrane when subject to a varying pressure. A curvature of inflatable membrane 102 may be created, for example, by varying the pressure of inflation fluid, by changing the size and orientation of inflatable tubelets 106, by providing membrane materials with a physical curvature bias, or through dissimilar membrane materials or thicknesses. The incorporation of such preferential bias or orientation into the membrane may enhance the therapeutic benefit and clinical healing response by creating a naturally contouring shape around the lung which facilitates drainage of collected and pooling fluid.

Pleural drainage catheter system 100 as disclosed may be used as a discreet device as described above, but preferentially is part of complete pleural drainage system, which will be further described herein.

The system 100 would solve the problem of inadequate pleural drainage by providing multiple drainage channels during the continuous or selective inflation of the inflatable membrane. Additionally, the inflation of the inflatable membrane separates adjacent tissues limiting adhesion and fibrous formations. By controlling the timing sequence of the pleural drainage catheter system's inflation with respect to the pressure variations of the inflation and concomitant suction applied to the pleural cavity, an additional therapeutic effect may be realized that effectively exercises the lung tissue, thereby minimizing fluid leakage and pooling of fluid, which reduces the potential for infection to occur. Further, the incorporation of a preferential bias or orientation into the inflatable membrane may enhance the therapeutic benefit and clinical healing response. Additionally, the effectiveness of an adhesion limitation can be further enhanced by coating the inflatable membrane with one of several anti-adhesion coatings.

FIGS. 2-5 depict an alternate exemplary embodiment of a pleural drainage catheter system 200 in accordance with another aspect of the present invention. The pleural drainage catheter system 200 is configured to extend into a pleural cavity of a patient (not shown). As described above with respect to the embodiment of FIG. 1, pleural drainage catheter system 200 includes an inflatable membrane 202 and a drainage catheter 204 integrally coupled to inflatable membrane 202. Inflatable membrane 202 defines eight tubelets 206 which when inflated define six passages 208, though alternate numbers can be provided. Tubelets 206 extend in a direction angled at an acute angle with respect to an axis of drainage catheter 204.

Additionally, as described above with respect to the embodiment of FIG. 1, drainage catheter 204 defines a central drainage lumen 212 and a membrane inflation lumen 214. Membrane inflation lumen 214 has a closed distal end, so that inflation fluid can be maintained under controlled pressure for delivery to and removal from inflatable membrane 202. Drainage catheter 204 also includes a plurality of drainage openings 216 through which fluid is drawn into central drainage lumen 212 and thereby removed from the pleural cavity.

Inflatable membrane 202 also includes a plurality of drainage holes 218. Drainage holes 218 enable fluid on one external side of inflatable membrane 202 to pass to an opposite external side of inflatable membrane 202, so that the fluid can be drawn into central drainage lumen 212 and thereby removed from the pleural cavity. The plurality of drainage holes 218 are illustrated as side-to-side drainage holes, though alternative spacings can be provided. The plurality of drainage holes 218 are located within the passages 208 defined by the tubelets 206 of the inflatable membrane 202. However, if alternatively shaped portions of inflatable membrane 202 are inflated, drainage holes 218 may be located in areas consistent with such construction. The drainage holes 218 are located adjacent to the drainage catheter 204 to facilitate the removal of fluid from the pleural cavity of the patient. Drainage holes 218 may nonetheless be located anywhere on inflatable membrane 202. In such a design, drainage holes 218 may operate in conjunction with passages 208 to increase the drainage area covered by system 200 and to facilitate the passage of fluid to drainage catheter 204. The shape and size of drainage holes 218 may be chosen to optimize passage of fluid to drainage catheter 204.

FIGS. 2a, 3a, and 3b depict exemplary pleural drainage catheter system 200 in a deflated state. As described above with respect to the embodiment of FIG. 1, inflatable membrane 202 has a deflated state, in which the tubelets 206 are deflated. In this state, the two opposed layers 220 and 222 of inflatable membrane 202 are positioned substantially adjacent one another. Even while not inflated, inflatable membrane 202 still provides some means to track and drain fluid, by providing a space between the tissue of the pleural cavity through which fluid may pass. Additionally, even while not inflated, any therapeutic coatings and/or agents on inflatable membrane 202 can be dispersed or actively delivered through contact of inflatable membrane 202 with the pleural tissue while inserted.

FIGS. 2b, 4a, and 4b depict exemplary pleural drainage catheter system 200 in an inflated state. As described above with respect to the embodiment of FIG. 1, inflatable membrane 202 also has an inflated state, in which tubelets 206 are inflated. In this state, portions of the respective opposed layers 220 and 222, which form tubelets 206, are spaced apart from one another. The external surface of inflatable membrane 202, which when inflated forms tubelets 206, also defines passages 208 between the tubelets 206. Though illustrated as parallel channels, the design of passages 208 is dependent only on the space provided between the deflated and inflated portions of membrane 202, and may take any shape or size which facilitates the separation of tissue and/or the movement of fluid. The passages 208 may function as drainage channels such that when inflatable membrane 202 is in the inflated state, passages 208 facilitate the movement of fluid along the external surface of inflatable membrane 202 to drainage catheter 204 for removal from the pleural cavity. Therapeutic coatings and/or agents can also be dispersed or actively and selectively dispended in the inflated state through contact of inflatable membrane 202 with the pleural tissue.

Figure 5:
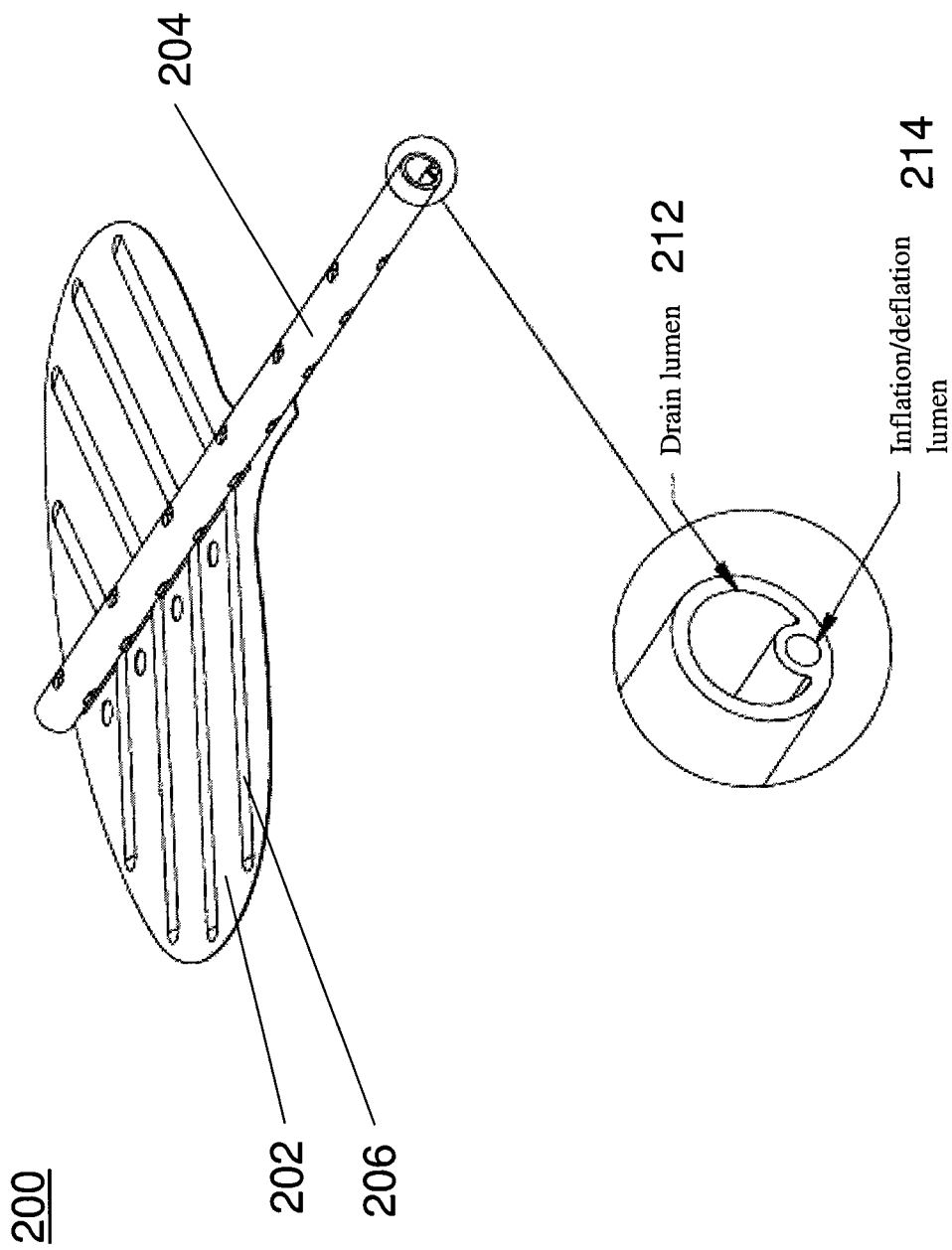
FIG. 5 is another perspective view of the pleural drainage catheter system shown in FIG. 2b.

FIG. 5 further depicts exemplary pleural drainage catheter system 200. Membrane inflation lumen 214 of drainage catheter 204 has an open proximal end. As will be described in greater detail below, membrane inflation lumen 214 is coupled for flow of inflation fluid through the open proximal end of membrane inflation lumen 214 to and from an interior of inflatable membrane 202. Membrane inflation lumen 214 may optionally be coupled for flow of inflation fluid through the open proximal end of membrane inflation lumen 214 to and from inflatable tubelets 206. In this configuration, the open proximal end of membrane inflation lumen 214 will be coupled to an external inflation system. The flow of inflation fluid through membrane inflation lumen 214 is then controlled by the external inflation system, as will be described later.

Membrane inflation lumen 214 is formed integrally with a wall of central drainage lumen 212 of drainage catheter 204. However, membrane inflation lumen may take any form within drainage catheter which keeps a flow of inflation fluid within membrane inflation lumen 214 separate from a flow of fluid being removed through central drainage lumen 212. Additionally, while membrane inflation lumen is illustrated as being within drainage catheter 214, a separate or adjacent membrane inflation lumen 214 can be provided.

Figure 6:
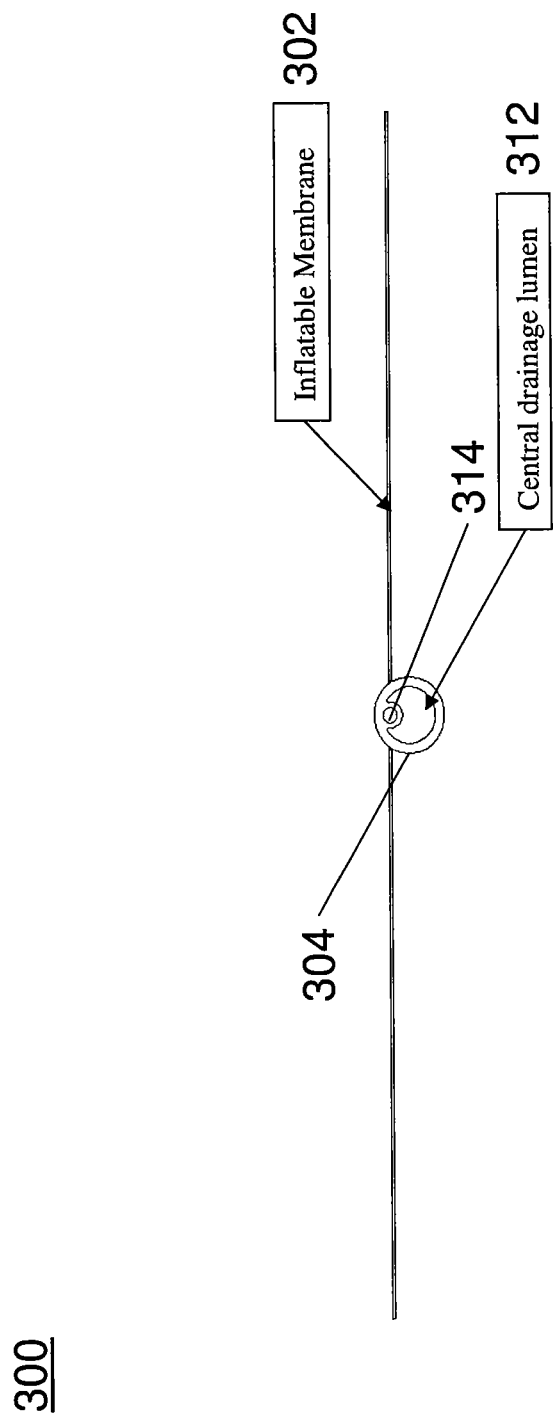
FIG. 6 is a cross-sectional end view of another exemplary embodiment of a pleural drainage catheter system in accordance with an aspect of the present invention.
Figure 7:
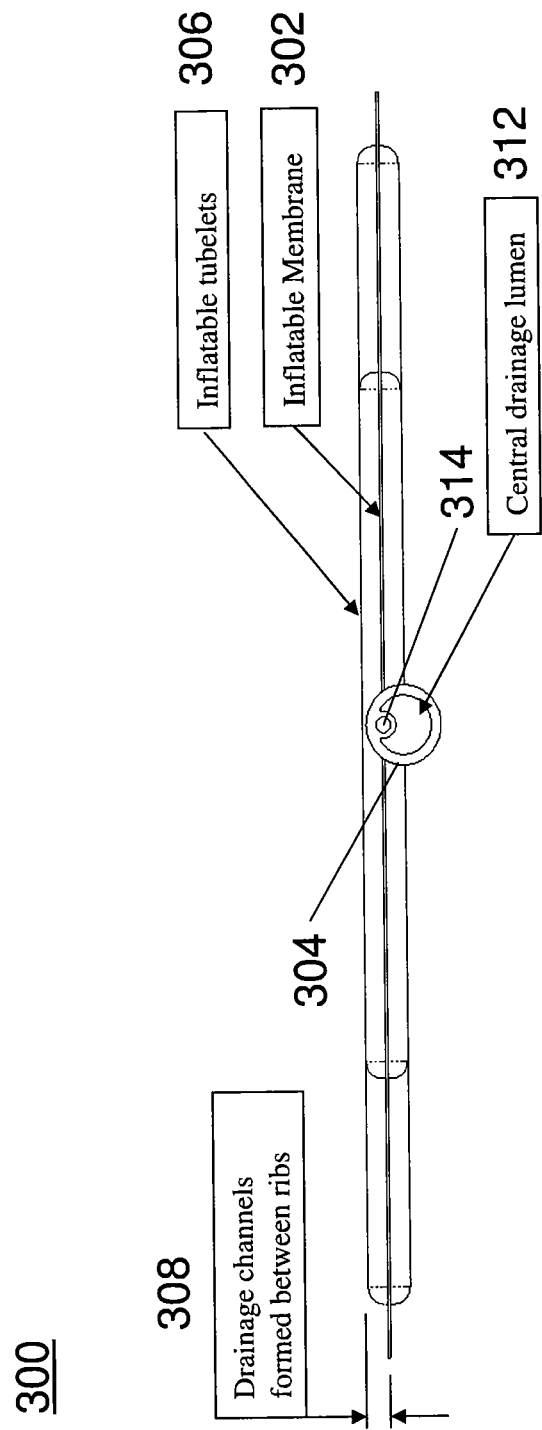
FIG. 7 is a cross-sectional end view of the pleural drainage catheter system shown in FIG. 6, in an inflated state.

FIGS. 6-7 depict an exemplary embodiment of a pleural drainage catheter system 300 in accordance with an aspect of the present invention. Pleural drainage catheter system 300 includes an inflatable membrane 302 and a drainage catheter 304 integrally coupled to inflatable membrane 302. In this embodiment, drainage catheter 304 is located below inflatable membrane 304 and is connected to inflatable membrane 304 such that inflatable membrane 302 covers a portion of the circumference of drainage catheter 304. However, it is contemplated that drainage catheter 304 may be coupled to inflatable membrane 302 in other configurations which similarly provide for a narrow insertion profile. Inflatable membrane 302 and drainage catheter 304 may be formed as one piece, or may be affixed together by RF welding, heat staking, or suitable adhesives.

As described in relation to the above embodiments, inflatable membrane 302 may define one or more tubelets 306 which when inflated define one or more passages 308. The passages 308 may function as drainage channels such that when inflatable membrane 302 is in the inflated state, passages 308 facilitate the movement of fluid along the external surface of inflatable membrane 302 to drainage catheter 304 for removal from the pleural cavity. Tubelets 306 may extend radially outward with respect to an axis of drainage catheter 304.

Drainage catheter 304 defines a central drainage lumen 312 and a membrane inflation lumen 314. Central drainage lumen 312 has an open distal end to provide a passage for the removal of fluid from the pleural cavity of the patient. Membrane inflation lumen 314 also has an open distal end, though its distal end is preferably closed so that inflation fluid can be maintained under controlled pressure for delivery to and removal from inflatable membrane 302. Membrane inflation lumen 314 is formed integrally with a wall of central drainage lumen 312 of drainage catheter 304.

Figure 10:
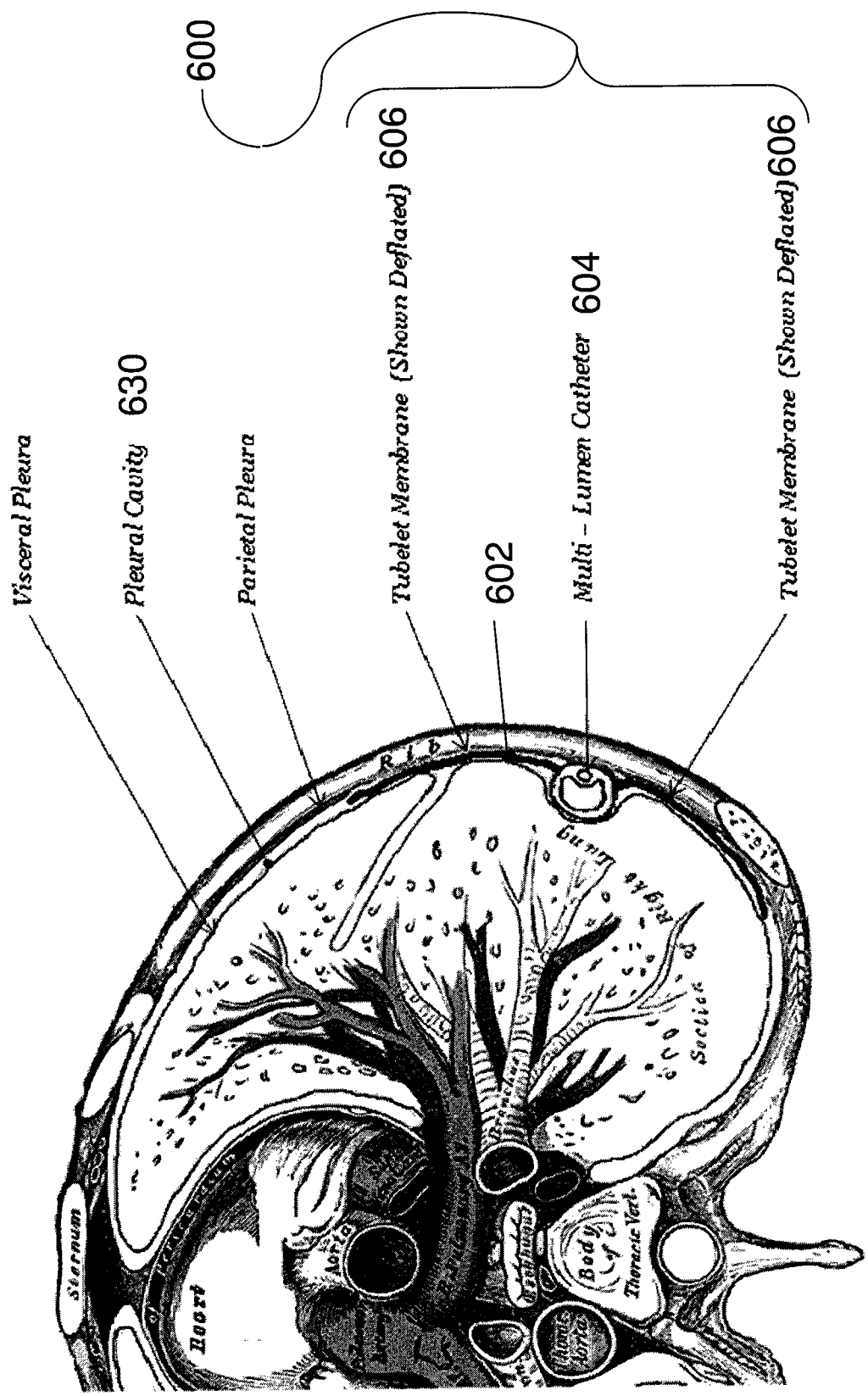
FIG. 10 is a cross-sectional end view of an exemplary embodiment of a pleural drainage catheter system inserted in a pleural cavity of a patient in accordance with an aspect of the present invention.
Figure 11:
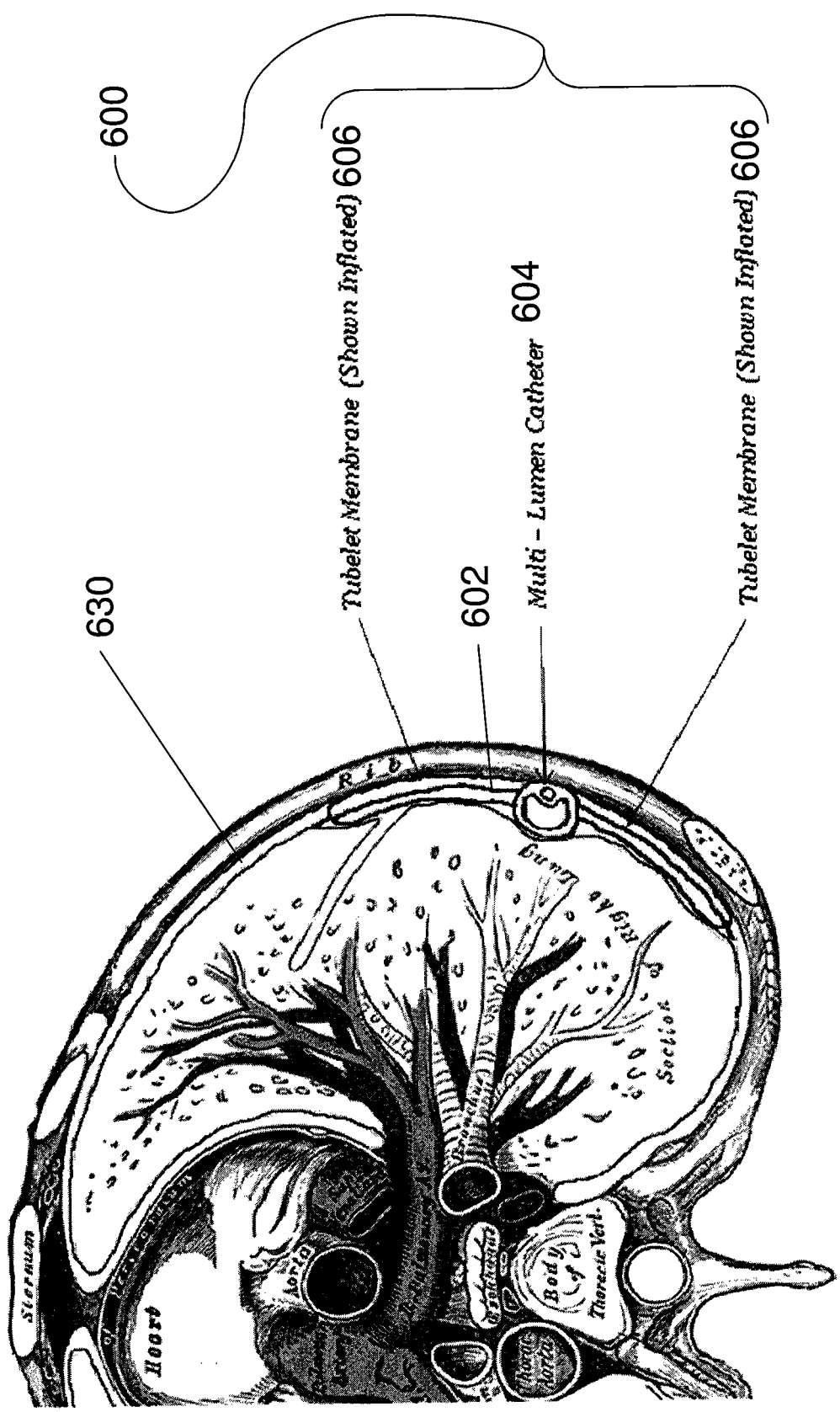
FIG. 11 is a cross-sectional end view of the pleural drainage catheter system shown in FIG. 10, in an inflated state.
Figure 12:
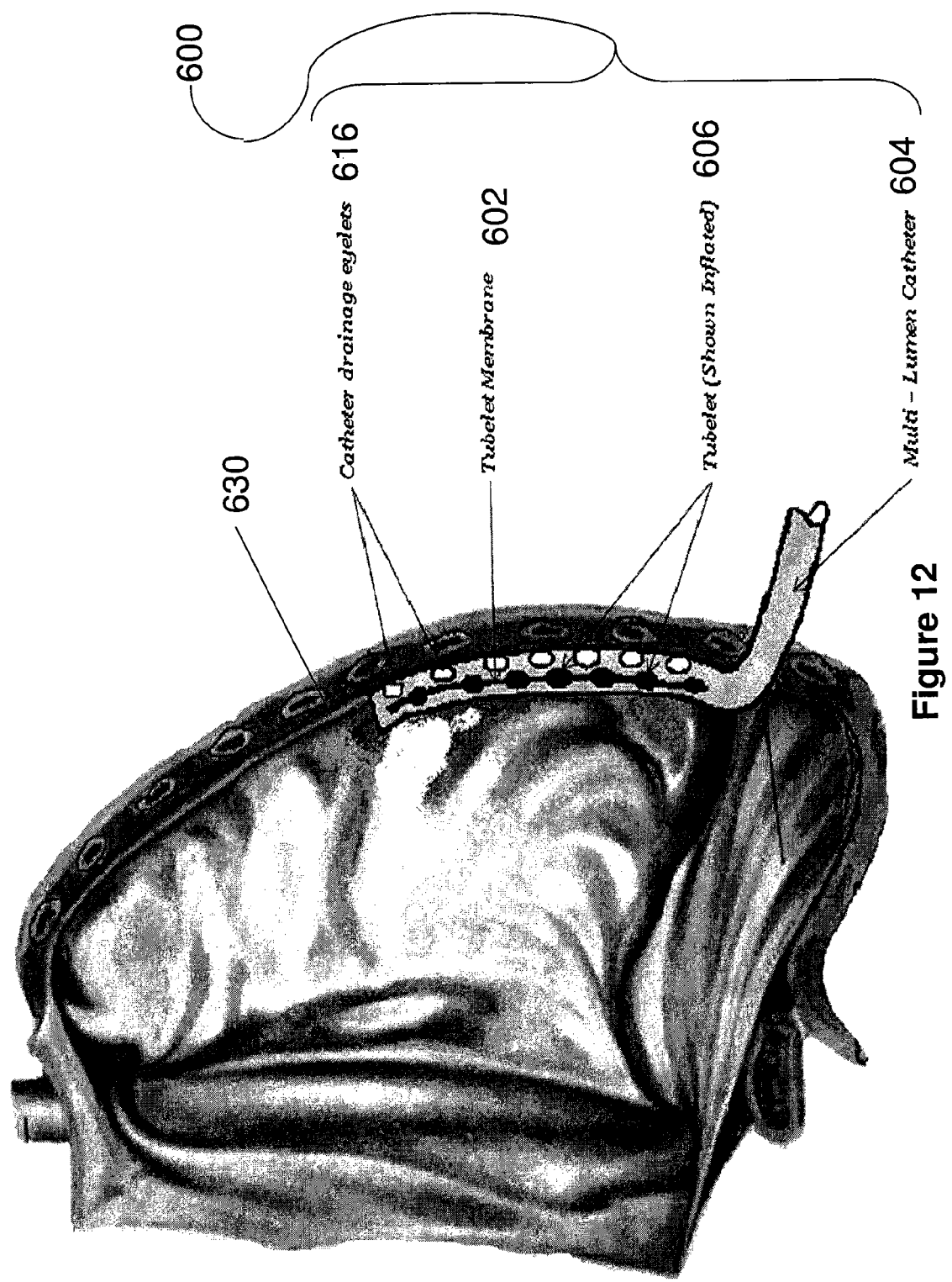
FIG. 12 is a side view of the pleural drainage catheter system shown in FIG. 11.

While FIGS. 6-7 illustrate the inflatable membrane 302 as planar in shape, the selected polymer material of inflatable membrane 302 can be such that the system 300 will conform to the anatomical constraints of the pleural space. As depicted in FIGS. 10-12, which are described below, the construction of inflatable membrane 302 may be such that the two opposing layers forming membrane 302 are made of materials or thickness to provide a preferential curve or bias of the membrane when subject to a varying pressure. A preferential curve may be created if one of the two opposing layers forming inflatable membrane 302 has slightly less area than the other layer. A curvature of inflatable membrane 302 may be created, for example, by varying the pressure of inflation fluid, by changing the size and orientation of inflatable tubelets 106, by providing membrane materials with a physical curvature bias, or through dissimilar membrane materials or thicknesses. The incorporation of such preferential bias or orientation into the membrane may allow inflatable membrane 302 to conform to the shape of the pleural cavity, and thereby enhance the therapeutic benefit and clinical healing response. Additionally, by controlling the inflatable tubelets 306 and their orientation, physical movement of drainage catheter 304 can be created which provides a sweeping effect of the catheter across and through the pulmonary space as it is inflated and deflated. By sequentially inflating and deflating tubelets 306 having different thicknesses and differently sized channels, or by inflating and deflating the tubelets 306 in stages, movement can be created which re-positions the catheter from one area to another within the pleural space or alternatively, can translate the catheter from one area to an adjacent area with minimal irritation or disruption of tissue.

Figure 8:
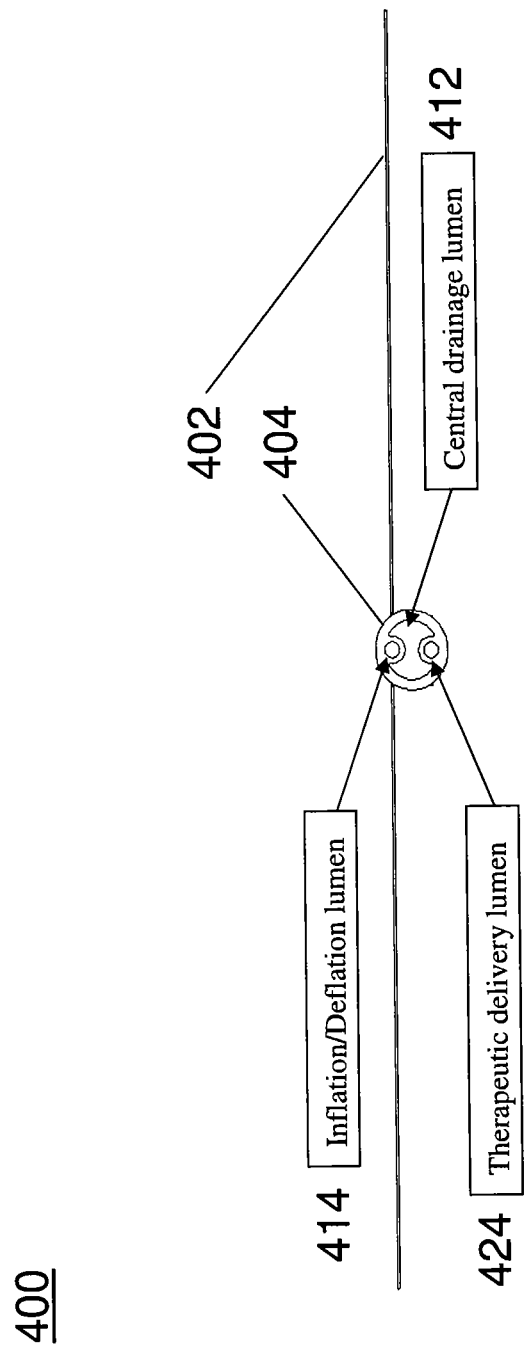
FIG. 8 is a cross-sectional end view of yet another exemplary embodiment of a pleural drainage catheter system in accordance with an aspect of the present invention.

FIG. 8 depicts an exemplary embodiment of a pleural drainage catheter system 400 in accordance with another aspect of the present invention. Pleural drainage catheter system 400 includes an inflatable membrane 402 and a drainage catheter 404 integrally coupled to inflatable membrane 402. Drainage catheter 404 defines a central drainage lumen 412 and a membrane inflation lumen 414.

Drainage catheter 404 further defines a delivery lumen 424 through which a medicament can be introduced into the pleural cavity and at least one delivery opening through which the medicament is delivered into the pleural cavity from the delivery lumen 424. The delivery opening is illustrated at the end of delivery lumen 424; however, the delivery opening may be located anywhere along delivery lumen 424. Additionally, delivery lumen 424 may have multiple delivery openings. Delivery lumen 424 may be a therapeutic delivery lumen for introducing medicaments into the pleural cavity. The medicaments introduced into the pleural cavity may include antibiotics or antimicrobial agents. Suitable antibiotics or antimicrobial agents will be known to one of ordinary skill in the art.

While delivery lumen 424 is depicted as a separate lumen for the delivery of therapeutic agents, this function may nonetheless be performed by other lumens of drainage catheter 404. For example, as would ordinarily be done during pleurodesis, central drainage lumen 412 may provide for the delivery of therapeutic agents to the pleural cavity in addition to providing a channel for the removal of fluid from the pleural cavity. Further, while delivery lumen 424 is depicted as an integral part of drainage catheter 424, it is contemplated that delivery lumen 424 could be defined by a separate catheter to optimize delivery of therapeutic agents to affected areas of the pleural tissue. Delivery lumen 424 may be located on any part of inflatable membrane 402. In addition, inflatable membrane 402 may contain an active fluid membrane that under sustained pressurization or over-pressurization may elute fluid or drugs to provide therapy to surrounding tissue in the pleural cavity to minimize inflammation or fibrous adhesion formation. The elution of fluid or drugs can be controlled by a membrane valve mechanism that activates when a predetermined pressure is reached. Alternatively, the porous characteristics of the membrane can be adjusted so that at a prescribed pressure, controlled weeping or leaking through the membrane occurs to deliver a medicament from the membrane pores. A variety of medicaments to therapeutically treat inflammation, pain, infection, and irritation can be delivered, such medicaments being known to one of ordinary skill in the art.

A benefit of medicament delivery through the drainage catheter or by an additional therapeutic delivery lumen in the drainage catheter tube is the ability to provide localized antibiotic or antimicrobial delivery, fibrin lysis therapy, or other analgesic therapy that can positively affect pulmonary dynamics, function and healing.

Figure 9:
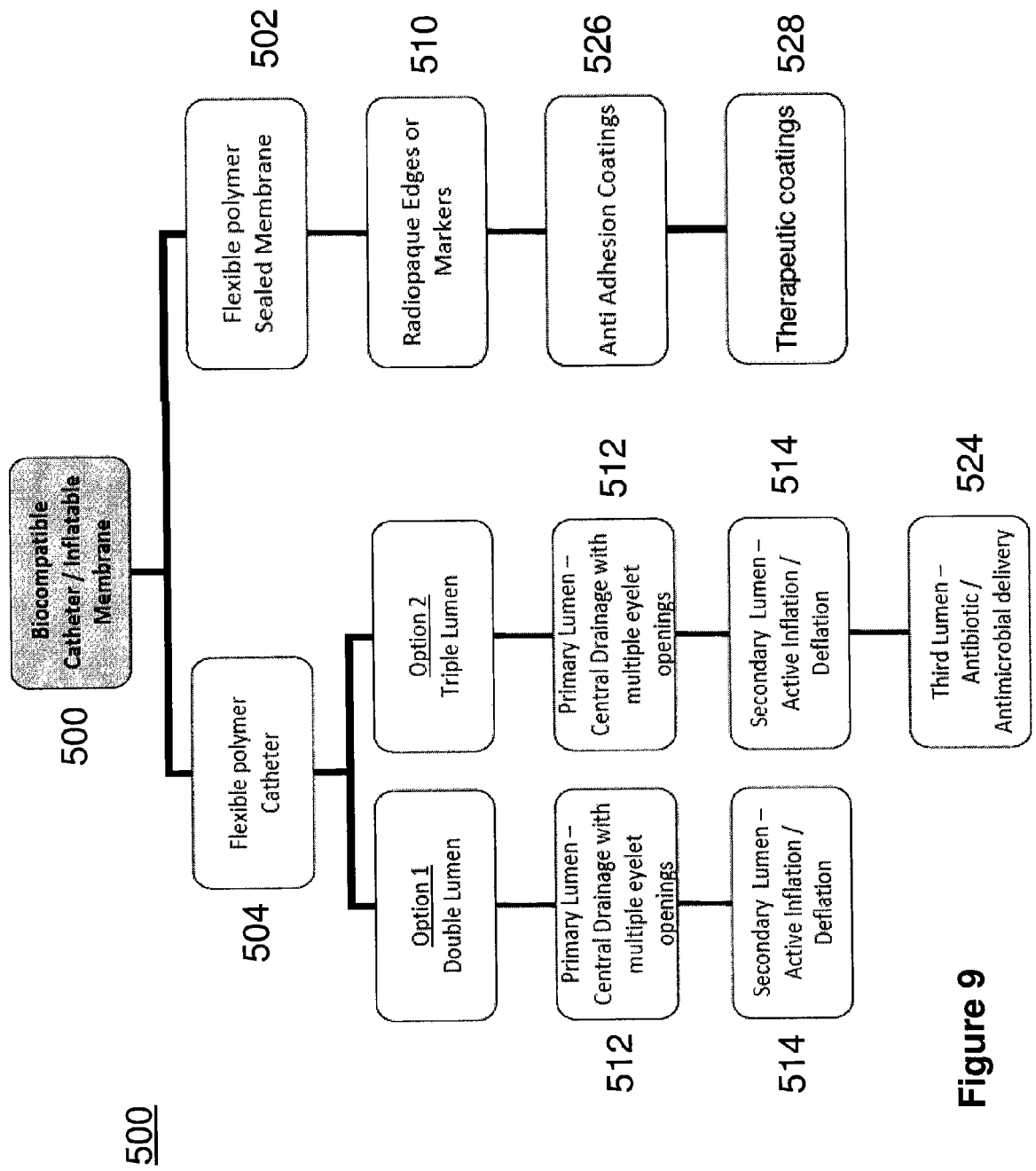
FIG. 9 depicts an embodiment of a pleural drainage catheter system hierarchy in accordance with an aspect of the present invention.

FIG. 9 is a pleural drainage catheter system hierarchy in accordance with an aspect of the present invention. Pleural drainage catheter system 500 includes an inflatable membrane 502 and a drainage catheter 504 integrally coupled to inflatable membrane 502. Inflatable membrane 502 may be a flexible polymer sealed membrane. Drainage catheter 504 may be a flexible polymer catheter.

Inflatable membrane 502 may also include radiopaque edges or markers 510 along the edges of inflatable membrane 502. The radiopaque markers 510 are positioned to facilitate visualization of inflatable membrane 502 during and after its insertion into the pleural cavity of a patient. Inflatable membrane 502 may further include an anti-adhesion coating 526 on the external surface of inflatable membrane 502 to resist adhesion of inflatable membrane 502 to tissue in the pleural cavity of a patient. Inflatable membrane 502 may further include a therapeutic coating 528 configured to provide therapy to tissue in the pleural cavity of a patient.

Drainage catheter 504 optionally defines two or three separate lumens. In a double lumen option, drainage catheter 504 defines a central drainage lumen 512 and a membrane inflation lumen 514. In this configuration, central drainage lumen 512 is the primary, or larger, lumen, and membrane inflation lumen 514 is the secondary, or smaller, lumen. However, membrane inflation lumen 514 need not be smaller than central drainage lumen 512; any size may be chosen for the lumens as necessary for their proper function. Central drainage lumen 512 includes multiple eyelet openings through which fluid is drawn into central drainage lumen 512 and thereby removed from the pleural cavity. Membrane inflation lumen 514 provides for active inflation and active deflation of inflatable membrane 502.

In a triple lumen option, drainage catheter 504 defines a central drainage lumen 512, a membrane inflation lumen 514, and a delivery lumen 524. In this configuration, central drainage lumen 512 is the primary, or larger, lumen, and both membrane inflation lumen 514 and delivery lumen 524 are secondary, or smaller, lumens. However, the secondary lumens need not be smaller than central drainage lumen 512; any size may be chosen for the lumens as necessary for their proper function. As with the double lumen option, central drainage lumen 512 includes multiple eyelet openings through which fluid is drawn into central drainage lumen 512 and thereby removed from the pleural cavity. Membrane inflation lumen 514 provides for active inflation and active deflation of inflatable membrane 502. Additionally, a medicament can be introduced into the pleural cavity of the patient through delivery lumen 524.

FIGS. 10-12 depict cross-sectional views of an exemplary embodiment of an inserted pleural drainage catheter in accordance with an aspect of the present invention. FIG. 10 depicts a cross-sectional end view of pleural drainage catheter system 600. Pleural drainage catheter system 600 is depicted inserted into the pleural cavity 630 of a patient. Pleural drainage catheter system 600 may be inserted into the pleural cavity 630 by means of a trocar system or other standard chest tube insertion techniques. Pleural drainage catheter system 600 includes inflatable membrane 602 and drainage catheter 604 integrally coupled to inflatable membrane 602. Inflatable membrane 602 is preferentially curved to conform to the anatomical constraints of the pleural cavity 630. In FIG. 10, inflatable membrane 602 is depicted in a deflated state.

FIG. 11 depicts another cross-sectional end view of inserted pleural drainage catheter system 600. In FIG. 11, inflatable membrane 602 is depicted in an inflated state. As will be discussed in detail below, inflatable membrane 602 of pleural drainage catheter 600 is inflated by the passage of inflation fluid through the membrane inflation lumen and into the inflatable portions or tubelets of inflatable membrane 602. This inflation fluid is provided by an inflation system which operates to actively inflate and deflate inflatable membrane 602 using the inflation fluid.

FIG. 12 depicts a cross-sectional side view of inserted pleural drainage catheter system 600. As in FIG. 11, inflatable membrane 602 is depicted in an inflated state.

Figure 13:
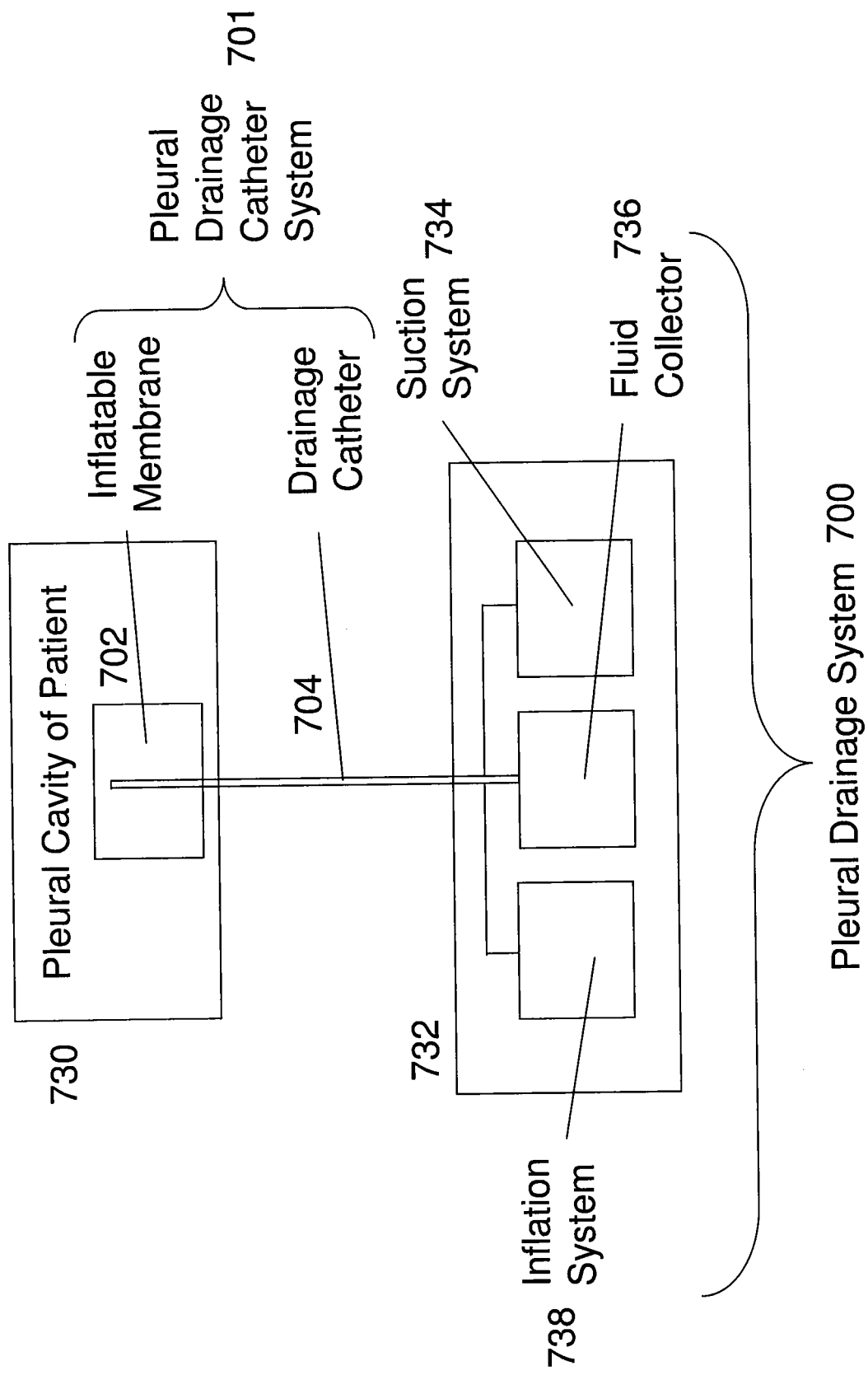
FIG. 13 depicts an embodiment of a pleural drainage system for draining fluid from the pleural cavity of a patient in accordance with an aspect of the present invention.

FIG. 13 depicts an exemplary embodiment of a pleural drainage system 700 in accordance with an aspect of the present invention. Pleural drainage system 700 is configured to deliver a therapeutic treatment to the pleural cavity 730 of a patient. Pleural drainage system 700 includes a pleural drainage catheter system 701. Pleural drainage catheter system 701 may include any of the features of the embodiments of pleural drainage catheter systems described above with reference to FIGS. 1-11. Pleural drainage catheter system 701 includes an inflatable membrane 702 having a deflated state and an inflated state and a drainage catheter 704 coupled to inflatable membrane 702. Drainage catheter 704 defines a central drainage lumen having a plurality of drainage openings through which fluid is drawn into the central drainage lumen from the pleural cavity 730, and an inflation lumen coupled for flow of inflation fluid to and from an interior of inflatable membrane 702.

In a preferred embodiment, pleural drainage system 700 comprises a collection and inflation means 732 configured with multiple pump and pressure sensors including a suction system 734, a fluid collector 736, and an inflation system 738, which will be described in greater detail below. Collection and inflation means 732 is optimally easily removable or connectable to pleural drainage catheter system 701 in order to form pleural drainage system 700. Collection means 732 is optimally self contained and/or configured to function on battery or direct wall power. Collection means 732 is illustrated as including a suction system 734, fluid collector 736, and inflation system 738. However, one or more of the systems may be omitted from collection means 732 and in that configuration may operate as a stand-alone system. Suction system 734 in means 732 may include a pump system to provide suction and pressure monitoring to drainage catheter 704. Fluid collector 736 in means 732 may be a receptacle for collecting fluid drained from pleural cavity 730 by drainage catheter 704. Fluid collector 736 may be configured to be easily removable and replaceable in collection means 732 for easy disposal of drained fluid. Inflation system 738 may include another pump/pressure system to provide modulated pressure and pressure detection to inflatable membrane 702. Collection means 732 may include further pump and pressure detection systems to facilitate the dispensation of therapeutic agents into the pleural cavity 730 of the patient.

Suction system 734 is connected to apply suction to the central drainage lumen of drainage catheter 704. This suction allows the central drainage lumen to draw fluid from the pleural cavity 730 into the drainage lumen of drainage catheter 704 through the drainage openings.

The benefit of suction system 734 applying suction to drainage catheter 704 in combination with inflatable membrane 702 is the facilitation of pleural drainage and thereby reduction of potential infection caused by trapped fluid in pleural cavity 730 of the patient. In operation, fluid which collects adjacent to drainage catheter 704 due to the passages formed by inflatable membrane 702. Fluid flows through the passages and is then drawn into drainage catheter 704 and removed from the pleural cavity. Additionally, suction system 734 may be configured to monitor the suction applied to the drainage lumen of drainage catheter 704.

Fluid collector 736 is coupled to receive fluid from the drainage lumen of drainage catheter 704. In this embodiment, fluid collector 736 is illustrated as coupled directly to drainage catheter 704. The fluid that is drawn into drainage catheter 704 may then flow directly into fluid collector 736 for collection and removal. Fluid collector 736 may alternately be coupled to suction system 734. In this configuration, suction system 734 may cause the fluid to flow into the suction system before being deposited in fluid collector 736. Fluid collector 736 may be formed integrally with suction system 734. However, fluid collector 736 is optimally a separately removable fluid collector for easy removal and disposal of drained fluid.

Inflation system 738 may include a pump configured for active inflation and active deflation of inflatable membrane 702. Inflation system 738 is connected to apply and modulate pressure to the inflation lumen of drainage catheter 704 and to deliver inflation fluid to the interior of inflatable membrane 702 through the inflation lumen defined by drainage catheter 704. Inflation fluid may be a liquid or gas. Suitable inflation fluids include air and saline solution, for example, but other inflation fluids can be substituted.

The suction applied by suction system 734 and the pressure modulations applied by the inflation system 738 may both be selectively engaged to run concurrently or discreetly. Preferably, both systems are selectively engaged as part of a therapeutic regimen to facilitate clinical healing. In one preferred embodiment, pleural drainage system 700 is activated in two stages. In the first stage, which follows successful insertion of pleural drainage catheter system 701, inflation system 738 is activated to allow inflatable membrane 702 to deploy into the pleural space. Radiopaque markers (not shown) may be used to determine or confirm the location and successful deployment of inflatable membrane 702. In the second stage, after successful deployment of inflatable membrane 702 is confirmed, inflation system 738 is switched into therapeutic mode, in which the active inflation and active deflation of inflatable membrane 702 occurs in short, low pressure cycles over a pre-determined period of time.

Additionally, drainage catheter 704 may selectively dispense therapeutic agents as part of this therapeutic regimen. Suitable therapeutic agents will be known to one of ordinary skill in the art.

Upon insertion of pleural drainage catheter system 701 into the appropriately selected region of pleural cavity 730, inflatable membrane 702 is discreetly and singularly inflated or connected to inflation system 738, which will then selectively inflate and then deflate inflatable membrane 702. The inflation/deflation sequence of inflatable membrane 702 separates the bounding layers of tissue and creates fissures and channels through which the fluid can be drawn to the centrally located drainage catheter 704. The collected and pooling fluid can then be drawn out of the pleural cavity and into fluid collector 736 by the suction applied to drainage catheter 704 by suction system 734. The timing of the inflation/deflation sequenced may be selected to optimize treatment of the pleural cavity.

Figure 14:
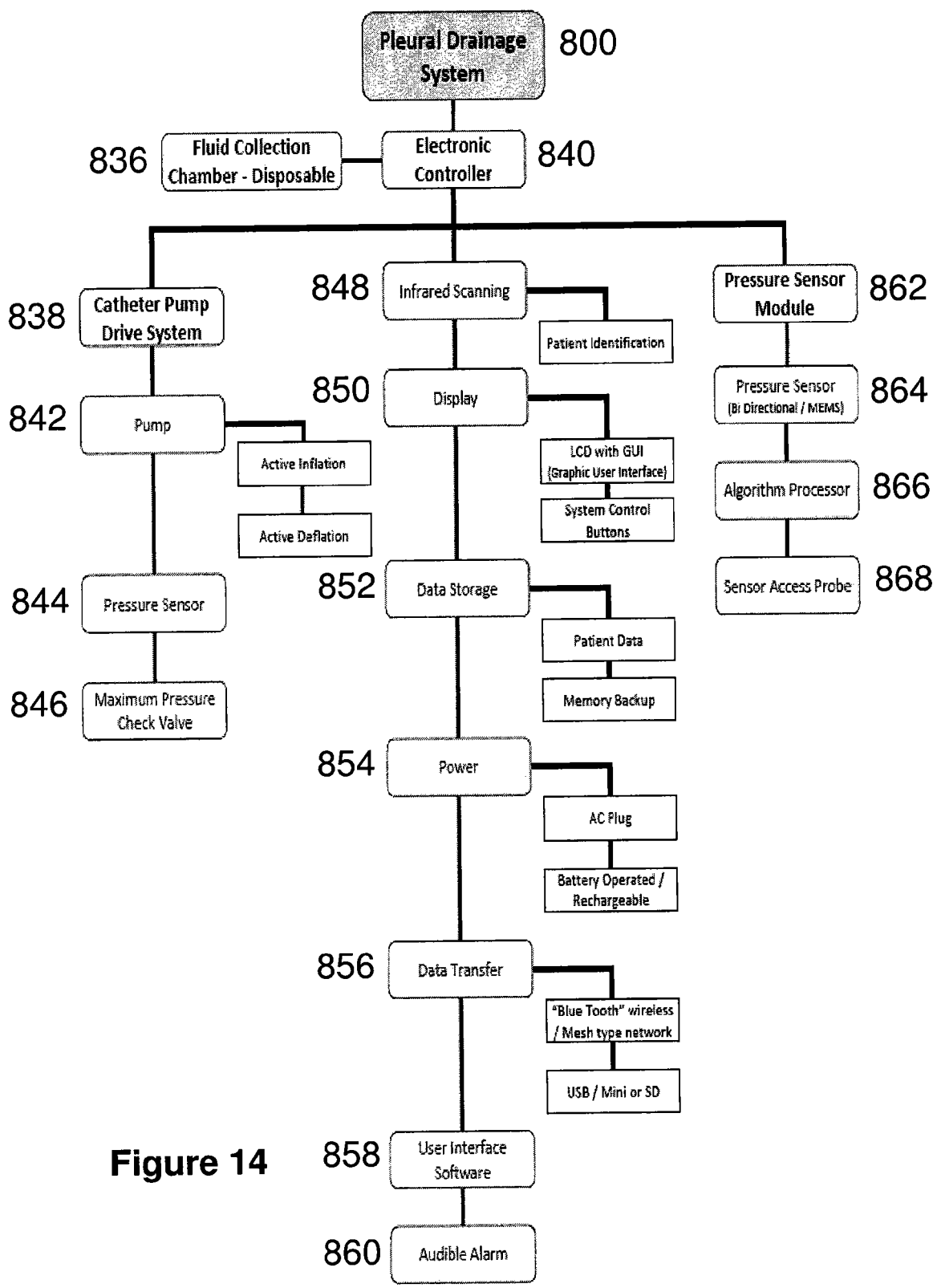
FIG. 14 depicts an embodiment of a pleural drainage system hierarchy in accordance with an aspect of the present invention.

FIG. 14 shows a pleural drainage system hierarchy in accordance with an aspect of the present invention. Pleural drainage system 800 may include any of the components described above with relation to FIG. 13. In a preferred embodiment, pleural drainage system 800 includes an electronic controller 840 coupled to either one or both of a suction system (not shown) and an inflation system 838. Electronic controller 840 may also be coupled to fluid collector 836. Fluid collector 836 may be a disposable chamber. Electronic controller operates and controls the various electronic and mechanical systems of pleural drainage system 800.

Inflation system 838 is optionally a catheter pump drive system containing an inflation fluid. Inflation system 838 includes a pump 842 configured for active inflation and active deflation of an inflatable membrane. Inflation system 838 may also include a sensor 844 configured to sense the pressure of the inflation fluid. Inflation system 838 may further include a maximum pressure check valve 846 configured to release inflation fluid from pleural drainage system 800 when a predetermined pressure is achieved.

Pleural drainage system 800 may further include a number of electronic components to be controlled by electronic controller 840. Pleural drainage system 800 may optionally include a scanner 848 for obtaining patient identification information. Pleural drainage system 800 may also include a display 850. Display 850 may be an LCD display having a graphical user interface (GUI). Display 850 may also include system controls configured to allow a user to control the operation of pleural drainage system 800. Pleural drainage system 800 may include a data storage means 852 for storing information including patient data and backup data. Data storage means 852 includes computer memory. Pleural drainage system 800 includes power means 854 including, for example, an A/C plug or batteries. Pleural drainage system 800 may include a data transfer means 856. Data transfer means 856 may be a connection such as a wireless communications device or a computer-readable removable disk. Pleural drainage system 800 may also include user interface software 858 to facilitate operation of pleural drainage system 800 and an audible alarm 860 for alerting a user. An alarm may be activated in conditions when, for example, pleural drainage system 800 detects a leak in the inflatable membrane, pleural drainage system 800 has a low battery or when the therapeutic session is over.

Pleural drainage system 800 also includes a pressure sensor module 862. Pressure sensor module 862 is configured to monitor the pressure of inflation fluid in the inflatable membrane. Pressure sensor module may be further configured to measure the exerted pressure within the pleural cavity. Pressure sensor module 862 may include a pressure sensor 864, a processor 866, and a sensor access probe 868.

The inflation system 838 and pressure sensor module 862 optimally incorporate a feedback means to measure the exerted pressure within the pleural cavity. By measuring the pressure exerted on the inflatable membrane within the pleural space, pleural drainage system 800 can be configured to determine the work output related to the exerted pressure as a function of the physiological conditions of the patient.

Additionally, as described below, the inflatable membrane may have inflated portions of different sizes, shapes, and locations. System 800 may further incorporate feedback means to measure the differential pressure across multiple areas of the inflatable membrane within the pleural cavity. Measuring the differential pressure in areas that are inflated to different volumes may provide feedback on the response and clinical condition of the tissue and other structures adjacent the inflatable membrane.

By measuring the pressure response of the patient, an algorithm can then be configured to optimize the sequence and timing of the inflation and deflation applied by inflation system 838 to the inflatable membrane. Additionally, inflation pressure exerted as well as duration of inflation and deflation can be selectively optimized so as to improve the healing response and pulmonary function of the patient.

Figure 15:
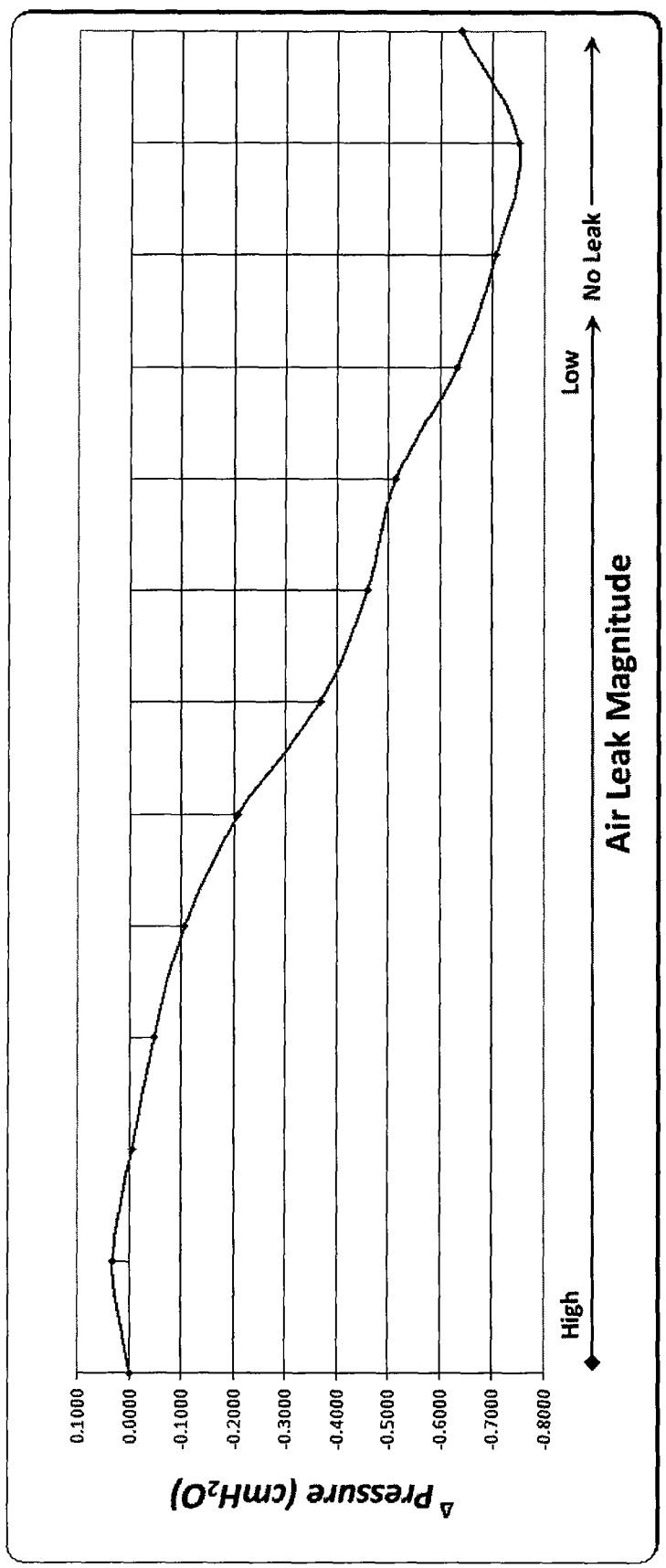
FIG. 15 is a graph depicting measurements of the decay in pressure in the pleural cavity of a patient as a function of time in accordance with an aspect of the present invention.

FIG. 15 is a graph depicting the pressure within the pleural space of a patient in accordance with an aspect of the present invention. The disclosed pleural drainage system may be configured and used to measure the pressure within the pleural space without restricting the flow in the drainage catheter. The rate of decay of the pressure in the pleural cavity correlates to the assessment of a patient airleak in the pleural cavity. Accordingly, the disclosed pleural drainage system may be used to monitor an airleak in a pleural cavity of a patient. Monitoring the airleak of the patient's pleural cavity can provide valuable information regarding treatment and recovery of the patient. This information may include providing the medical staff with increased knowledge and understanding on how a post-operative airleak is healing during patient recovery. This may further lead to establishing reliable data for pattern recognition for multiple patients to assist a doctor or medical practitioner in the consideration of when to remove a chest tube. This information in turn may potentially shorten the length of hospital stay a patient may require following thoracic surgery.

Airleaks within the pleural cavity are monitored by measuring the rate of pressure decay in the pleural cavity of a patient, correlating the rate of pressure decay to an associated airleak, and generating an indicator showing a trend in the magnitude of the airleak in the pleural cavity. As described above, the rate of exerted pressure decay in the pleural cavity of a patient may be measured using the disclosed pleural drainage system.

It has been discovered that the relationship of the trend in airleak resolution is proportional to the measured pressure decay and can be expressed by the following relationship:

$$Q_{Airleak} \alpha \int P dt$$

where:

$Q_{Airleak}$ is an extrapolated airleak,

P is a measured pressure, and t is time.

Accordingly, the patient airleak correlates to the rate of pressure decay in the pleural space of the patient.

Figure 16:
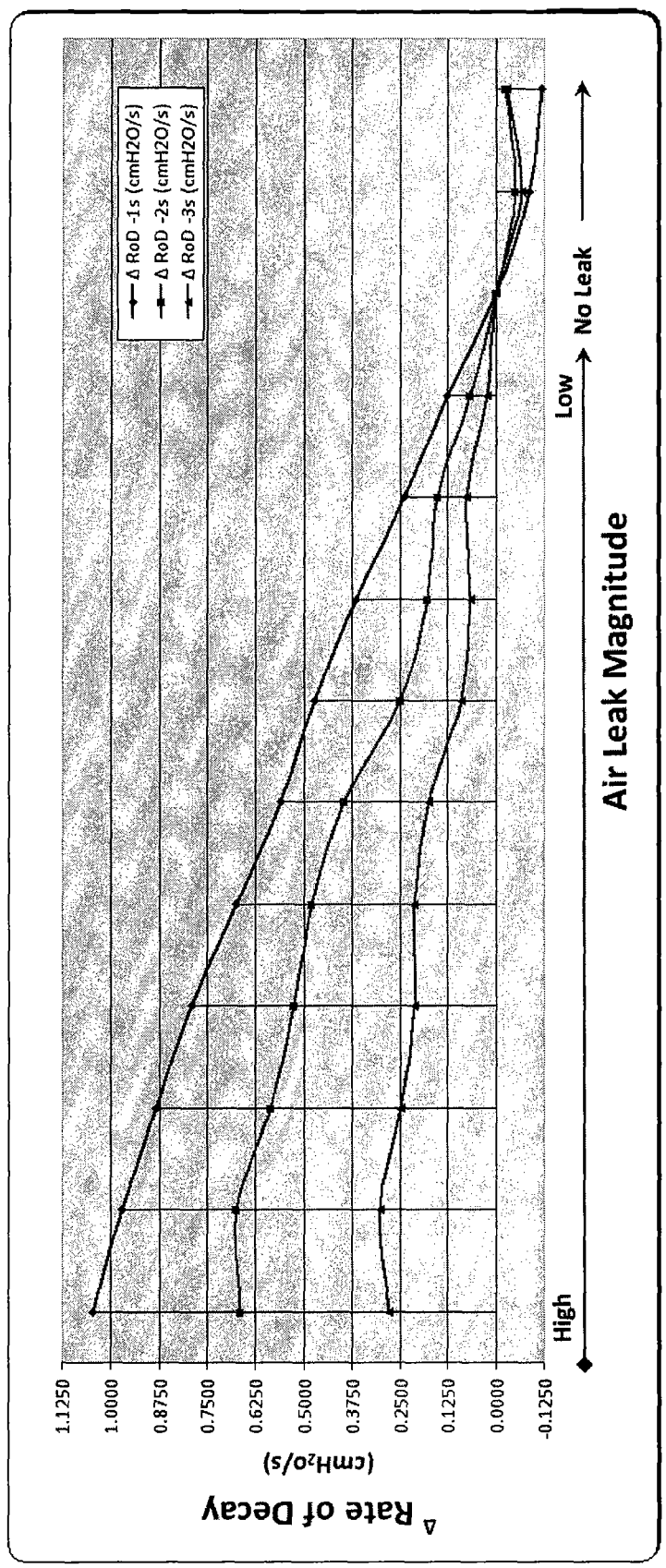
FIG. 16 is a graph depicting the trend and rates of pressure decay relating to an associated patient airleak as a function of time in accordance with an aspect of the present invention.

FIG. 16 is a graph depicting the rate of pressure decay within the pleural space of a patient in accordance with an aspect of the present invention. Using the above correlation, the pleural drainage system is able to quantify the trend and rate of decay as a function of airleak over differing time intervals. Changes and resolution of the patient airleak as a function of clinical healing are detected by a reduction in the measured pressure decay rate, and can then be correlated to a reduced airleak by the above algorithm.

An indicator can be generated depending on the variation in patient airleak. For example, the change in pressure decay and proportional correlation to airleak variation can be accumulated and the feedback presented by a varying trend analysis. The generated indicator may include a simple light means where a reduction in airleak over a determined period of time correlates to a change in the emitted light. According to one exemplary embodiment, this includes a progressive Red to Yellow to Green light indication. In this embodiment, the progressive change in the light color provides the clinician with information related to the reduction in the airleak and improvement of the overall pleural health of the patient.

It will be understood that pleural drainage systems of the present invention are not limited to the features described. Additional features of exemplary embodiments of pleural drainage systems are described herein with reference to FIGS. 17-23.

Figure 17:
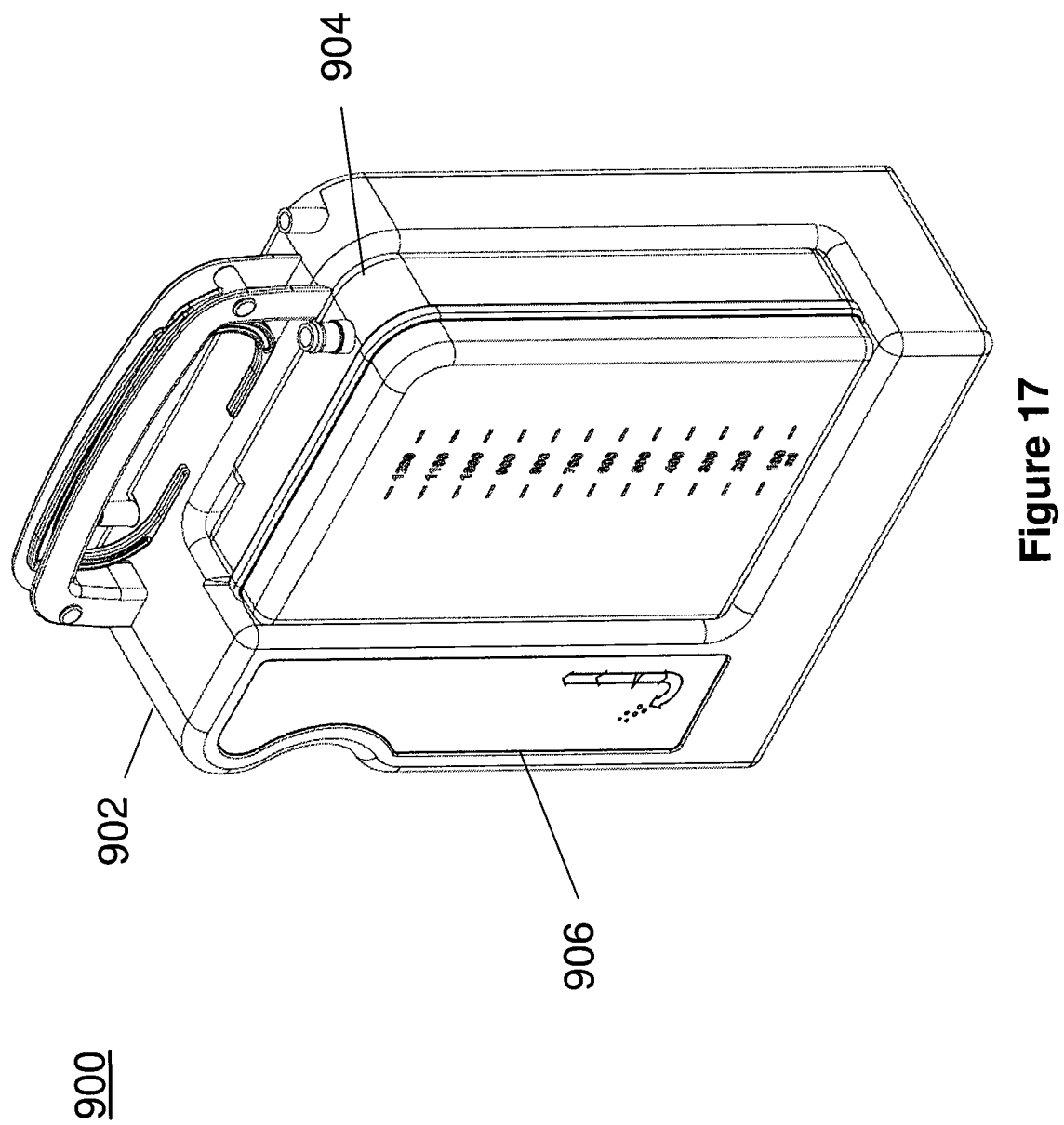
FIG. 17 depicts another embodiment of a pleural drainage system for draining fluid from the pleural cavity of a patient in accordance with an aspect of the present invention.

In the exemplary embodiment illustrated in FIG. 17, a pleural drainage system 900 includes a suction system 902 and a fluid collector 904. The suction system 902 may be coupled to provide suction to a drainage catheter (not shown). As will be described herein, suction system 902 may generate suction using one or more pumps or may be coupled to an external source of suction (i.e., a hospital suction line) in order to provide suction to the drainage catheter. Any suitable drainage catheter can be selected for use with suction system 902.

Fluid collector 904 may be coupled to receive fluid from the drainage catheter. As illustrated in FIG. 17, fluid collector 904 may be a sub-component that is configured to be removed from suction system 902 to facilitate the removal and/or disposal of fluid.

Suction system 902 includes a control panel 906 disposed on a front surface of suction system 902. Control panel 906 may include a plurality of controls for operating pleural drainage system 900. Exemplary controls and indicators of control panel 906 are described with reference to FIG. 18.

Pleural drainage systems in accordance with the present invention preferably include a system on/off switch. In an exemplary embodiment illustrated in FIG. 18, control panel 906 includes an on/off switch 910. On/off switch 910 may be operable to activate or deactivate the suction system 902 of the pleural drainage system 900. On/off switch 910 may include an LED that indicates when the pleural drainage system 900 is active. For example, the LED may continuously blink when the pleural drainage system is active, and may be turned off when the pleural drainage system is not active.

Figure 18:
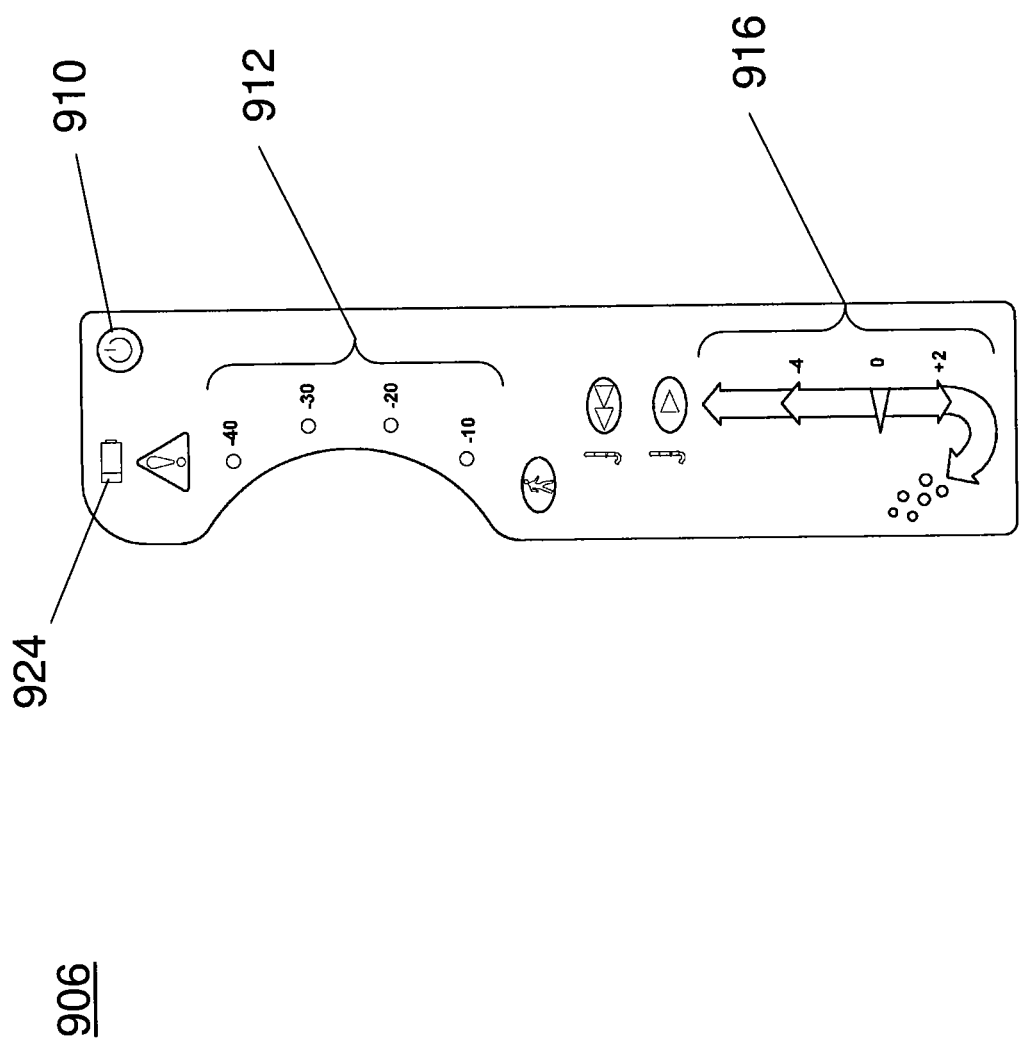
FIG. 18 depicts a control panel of the pleural drainage system shown in FIG. 17.

Pleural drainage systems may further include a vacuum suction indicator. In an exemplary embodiment, control panel 906 includes a vacuum suction indicator 912, as illustrated in FIG. 18. Vacuum suction indicator 912 may function when an external suction source is utilized by suction system 902, or when suction is provided internally by suction system 902. Vacuum suction indicator 912 may desirably indicate the target vacuum pressure to be applied to the patient. For example, indicator 912 may include four target pressures to be applied to the patient, e.g., −10, −20, −30, −40 cmH$_2$O. Each of the four target pressures may be identified by an LED on control panel 906, as illustrated in FIG. 18. The four target pressures represent one preferred embodiment but other target pressures, e.g., −5 up to −200 cmH$_2$O are also within the clinically significant range for the described device and may be added or substituted. Additionally, while four target pressures are described, any number of target pressures can be selected.

The operator of pleural drainage system 900 may employ vacuum suction indicator 912 to select a target pressure to be applied to the patient. For example, pleural drainage system 900 may include a mechanical dial regulator to allow an operator to mechanically adjust the target pressure provided by suction system 902. Suction system 902 may then control the suction provided to the patient based on the selected target pressure.

Pleural drainage systems may further include a controller module for controlling the suction provided to a drainage catheter. The controller module preferably includes a vacuum sensor for measuring the negative pressure applied by the suction system.

Figure 19:
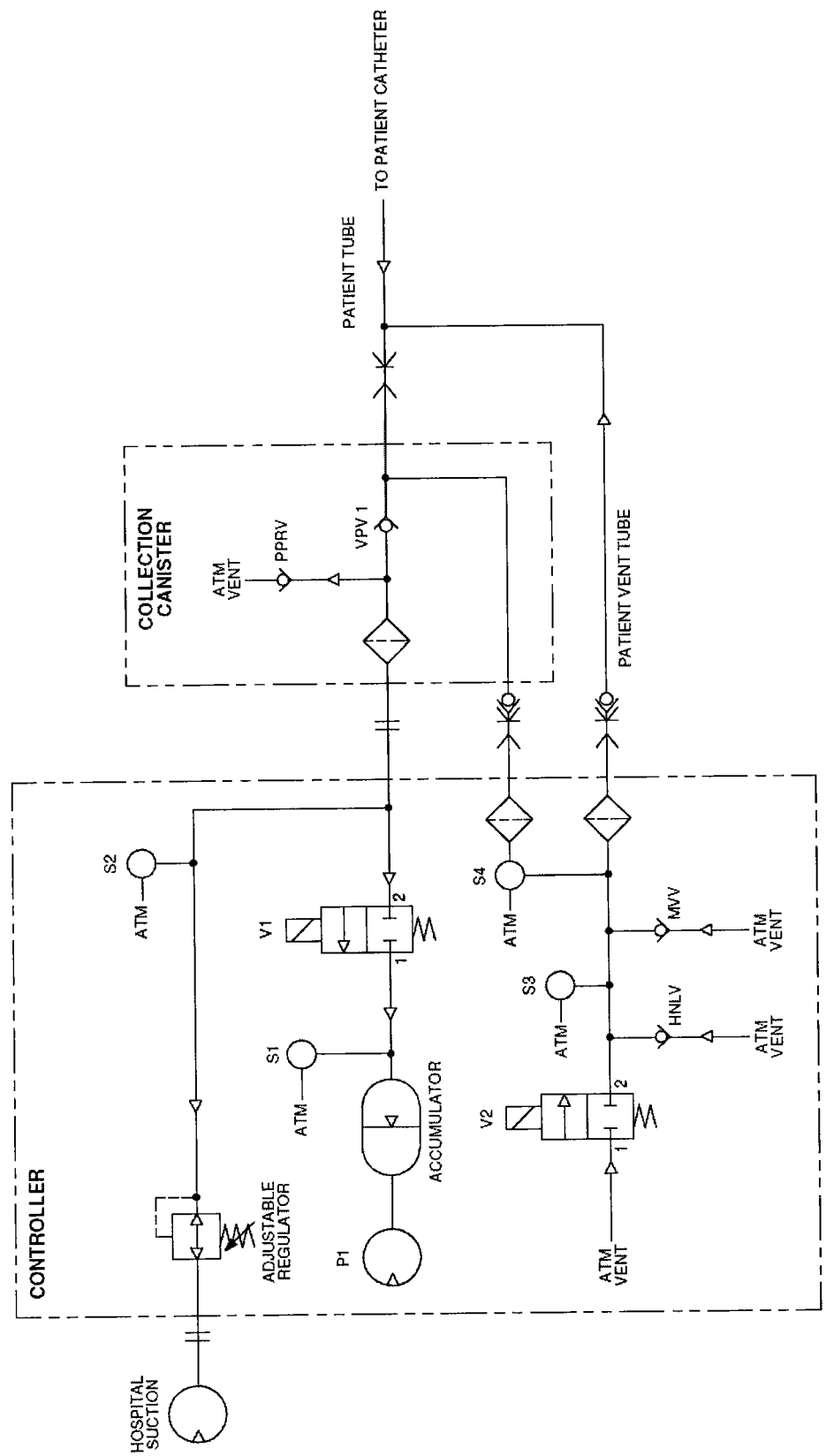
FIG. 19 is a schematic diagram illustrating an exemplary arrangement of electrical components that can be used in the pleural drainage system shown in FIG. 17.

In an exemplary embodiment, the controller module of pleural drainage system 900 includes a vacuum sensor S2, as illustrated in the schematic diagram in FIG. 19. Vacuum sensor S2 measures the negative pressure provided by suction system 902. Vacuum sensor S2 may further operate in conjunction with vacuum suction indicator 912 to indicate the measured negative pressure. For example, as described above, indicator 912 may include four LEDs that correspond to target pressures.

Pleural drainage system 900 may illuminate one of the LEDs of vacuum suction indicator 912 when the measured pressure is within a predetermined range of the target pressure of the corresponding LED. For example, LEDS of vacuum suction indicator 912 optionally blink when the vacuum pressure measured by sensor S2 is within +/−3 cmH$_2$O of the set target pressure. Further, the nearest corresponding LED to the set target vacuum pressure outside the +/−3 cmH$_2$O tolerance range may be set to illuminate until the target set vacuum pressure is within range.

To accurately detect the range of negative pressures generated by suction system 902, vacuum sensor S2 may optionally measure pressures in the range from "0" to "−1" PSI (or approximately "0" to "−70.3 cmH$_2$O"). Suitable vacuum sensors for use with the present invention include Model No. HSCMRNN001PGAA3, provided by Honeywell International Inc., although other suitable vacuum sensors are optionally selected.

Pleural drainage systems may also include a patient pressure indicator. In an exemplary embodiment, control panel 906 includes a patient pressure indicator 916, as illustrated in FIG. 18. The operation and function of the patient pressure indicator will be described below. The shape, size and configuration of the patient pressure indicator 916 can be varied to provide any one of many shapes, sizes and configurations, depending on aesthetic preferences and the desired ornamentation of the drainage system.

As described above, pleural drainage systems optionally employ an algorithm, such as the one described above, to determine a patient's airleak. Pleural drainage system 900 may employ patient pressure indicator 916 as described above to indicate the patient airleak to an operator.

As described above, pleural drainage systems preferably include a pressure sensor. In an exemplary embodiment, the controller module of pleural drainage system 900 includes a pressure sensor S3, as illustrated schematically in FIG. 19. Pressure sensor S3 may be connected in line with the drainage catheter of the pleural drainage system in order to measure pressure in the patient line. The pressure sensor S3 is optionally configured to measure the peak pressure during expiration and inspiration of the patient at each breath cycle. System 900 may further illuminate one or more of the LEDs of patient pressure indicator 916 that correspond with the range of pressure assigned to such LED, as will be described below.

Figure 20:
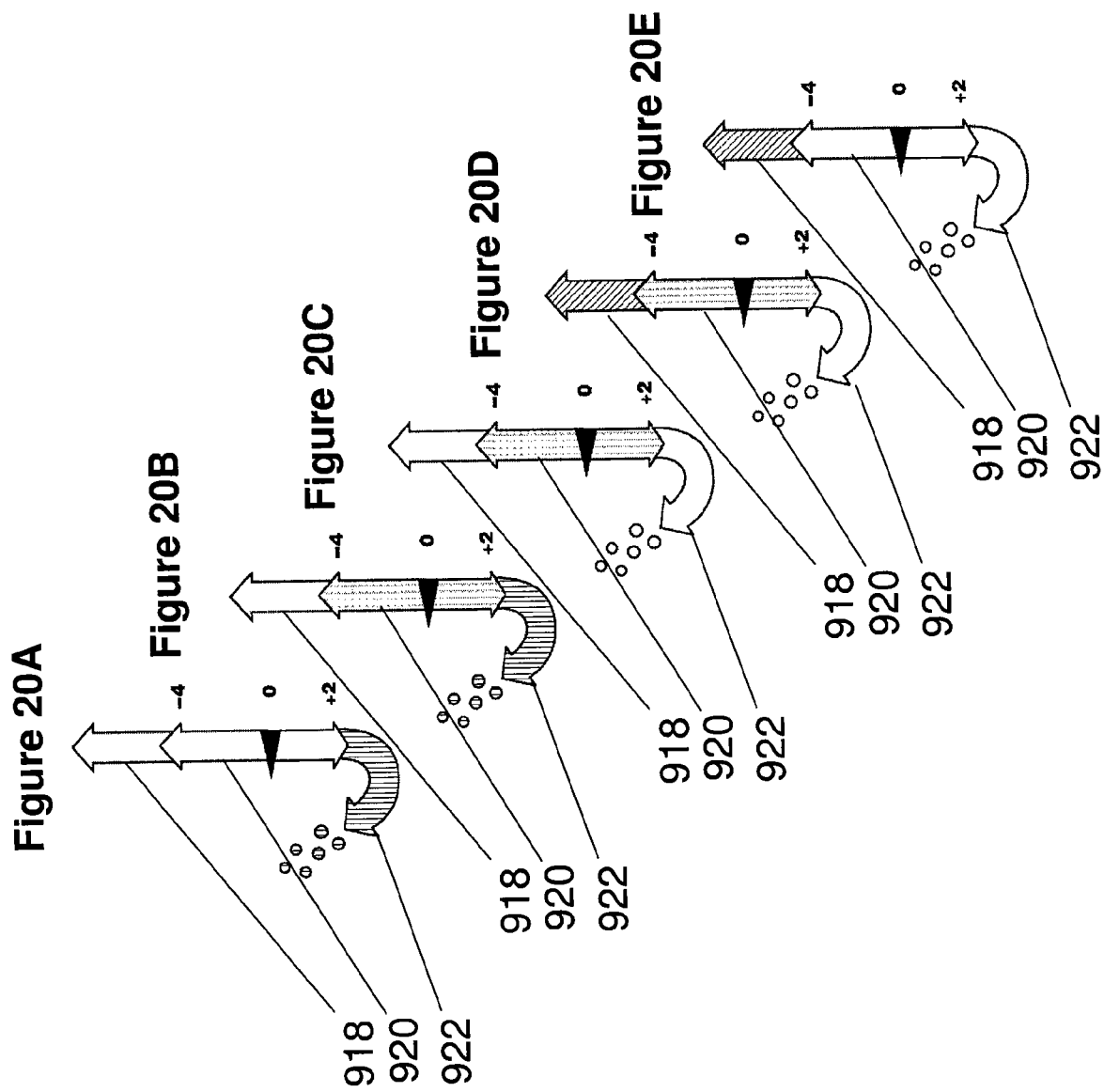
FIG. 20 depicts exemplary patient pressure indicators of the control panel of the pleural drainage system shown in FIG. 17.

Patient pressure indicator 916 includes three LEDs to provide indication of a patient's pleural pressure, measured by pressure sensor S3, to an operator of pleural drainage system 900, as illustrated in FIG. 20. Though FIG. 20 illustrates an embodiment having three LEDs, a smaller or larger number of LEDs or other indicators are optionally selected. Also, the appearance (shape, size and configuration) of the indicators can be modified depending on aesthetic and ornamental considerations.

For example, as described above, patient pressure indicator 916 may include a green LED 918, a yellow LED 920, and a red LED 922, the color differences being indicated symbolically by cross-hatching in FIG. 20. LEDs 918-922 may be illuminated when the measured pressure, or a measured or calculated pressure differential, is within certain thresholds. In an exemplary embodiment, patient pressure indicator 916 activates a blinking green LED 918 to indicate that the pleural cavity is at optimum sub-atmospheric pressure, and/or that there is no patient airleak. Patient pressure indicator 916 may activate a blinking yellow LED 920 to indicate that a pleural cavity is at minimal positive and low sub-atmospheric pressure, and/or that there may be no patient airleak. Finally, patient pressure indicator 916 may activate a blinking red LED 922 to indicate that a pleural cavity is at positive pressure, and/or that there is a patient airleak.

Presence of a patient airleak may be determined using the algorithms described above. Specifically, it may be determined based on variables including one or more of a measured pressure, a change in measured pressure over time, and other inputs based on the patient's condition at a particular time or over a particular period of time.

When no suction is provided by pleural drainage system 900, the thresholds for illuminating LEDs 918-922 may be determined based on expected clinical patient pressures. For example, patient pressure indicator 916 may be configured to illuminate only the red LED 922 when the patient's pressure is +0.5 $cmH_2O$ or greater, as illustrated in FIG. 20A. Patient pressure indicator 916 may be configured to illuminate only the yellow LED 920 when the patient's pressure is between 0 and −3.90 $cmH_2O$, as illustrated in FIG. 20C. Patient pressure indicator 916 may be configured to illuminate only the green LED 918 when the patient's pressure is −4.00 $cmH_2O$ or less, as illustrated in FIG. 20E. While patient pressure indicator 916 is illustrated as including pressure thresholds of −4 $cmH_2O$ and +2 $cmH_2O$, it will be understood that any other values can be selected for these thresholds, as described below.

When suction is provided by pleural drainage system 900, the pressure thresholds for illuminating LEDs 918-922 may be determined based on both expected clinical patient pressures and suitable pressure differentials between the patient line and the fluid collector 904. For example, as described above, the controller module of pleural drainage system 900 may include a pressure sensor S3 for measuring a pressure in the patient line. The controller module may further include a pressure sensor S4 for measuring a pressure in the fluid collector 904. The controller module may be operable to determine a pressure differential between the patient line and the fluid collector.

In such a configuration, patient pressure indicator 916 may be configured to illuminate only the red LED 922 when a decay in pressure is measured (corresponding to a patient airleak), as illustrated in FIG. 20A. Patient pressure indicator 916 may be configured to illuminate only the yellow LED 920 when a minor or substantially no pressure decay is measured (corresponding to when there may or may not be an airleak), as illustrated in FIG. 20C. Patient pressure indicator 916 may be configured to illuminate only the green LED 918 when there is no decay in the pressure and no pressure differential (corresponding to no patient airleak), as illustrated in FIG. 20E.

It will be understood that these thresholds are illustrative and not limiting, and that intermediate ranges could be established between these thresholds, such that patient pressure indicator 916 may illuminate in five stages instead of three, for example. In this case, patient pressure indicator 916 may illuminate both red and yellow LEDs 922 and 920, as illustrated in FIG. 20B. It may also illuminate both yellow and green LEDs 920 and 918, as illustrated in FIG. 20D. These additional conditions for LEDs 918-922 provide additional information indicative of the status of a patient's air leak.

Again, the appearance of the patient pressure indicator 916 and LEDs 918-922 can take a wide variety of forms while still providing an indication of the status of a patient. For example, the LEDs can be replaced by other means for visually indicating the status of a patient's air leak. Also, the shape, orientation, position, and size of the indicators can be modified, and their positions with respect to one another can also be modified, depending on aesthetic considerations while providing the same function. Ornamental features of patient pressure indicator 916 are described separately in U.S. Design patent application Ser. No. 29/357,469, filed Mar. 12, 2010.

Pleural drainage systems in accordance with aspects of the present invention may further include a low battery indicator. In an exemplary embodiment, control panel 906 includes a low battery indicator 924 as illustrated in FIG. 18. Low battery indicator 924 may be configured to blink when the pleural drainage system 900 has less than a predetermined power (such as 20% battery power for example) remaining.

Pleural drainage systems according to embodiments of this invention may also include an audible alarm. In an exemplary embodiment, control panel 906 includes an audible alarm (not shown). The audible alarm may operate in conjunction with the low batter indicator 924, such that the audible alarm beeps periodically when the battery power is low, or when the pleural drainage system 900 needs to be connected to AC power. The audible alarm may also operate in conjunction with the fluid connector 904 to indicate when the fluid connector 904 is full and should be removed/replaced.

Pleural drainage systems in accordance with aspects of the present invention may further include a fluid-clearing device. In an exemplary embodiment, pleural drainage system 900 includes a fluid clearing device, as illustrated schematically in FIG. 19. The fluid clearing device removes fluid or blockages from within a patient tube automatically when a predefined pressure differential exists between the measured pressure at the patient (from pressure sensor S3) and the measured pressure within the fluid collector (from pressure sensor S4). Alternatively the fluid clearing device can be activated based on a fixed or selectable timer.

The fluid-clearing device includes an accumulator and a vacuum pump P1, as illustrated schematically in FIG. 19. When the fluid-clearing device is activated, the accumulator will have its air volume drawn down to −600 $cmH_2O$ negative vacuum pressure using vacuum pump P1. A vacuum sensor 51 inline with the fluid collector 904 may be used to determine the pressure of the accumulator and shut off the pump P1 when the accumulator reaches the desired negative pressure. The fluid-clearing device may also include a microcontroller for controlling the activation of the accumulator.

The accumulator may be closed off by a magnetic valve V1 in order to store the energy (−600 $cmH_2O$) within the accumulator until the magnetic valve is signaled to activate. Valve V1 may be activated when the differential pressure measured between pressure sensor S3 and pressure sensor S4 reaches a predefined differential pressure, at which time the stored energy will be released from the accumulator while simultaneously opening a separate vent valve V2 to allow the fluid within the patient tube to flow into the fluid collector 904. Opening vent valve V2 may allow differential pressure to enter at the patient tube, thereby preventing exposure of the patient to high negative pressure. The stored negative pressure from the accumulator will draw the fluid away from the patient and into the fluid collector 904. Alternatively, the accumulator stored pressure may be adjusted by the algorithm described above, and set point values other than −600 cmH$_2$O may be utilized as determined to be most clinically relevant. Additionally, the accumulator stored pressure may be adjusted based on desired power usable by pump P1 and necessary negative pressure for removing a blockage.

It may be desirable to clear the patient tube in order to assure accurate volumetric measurement of the collected fluid by preventing fluid collected within the tube from not being recorded, which may create variability in the clinical assessment of the collected drainage. It may also provide clinical benefit by keeping the tube clear so as to facilitate further drainage and to minimize the backpressure created to a patient trying to expel an air leak. This feature may also minimize care and effort for the clinical staff.

Vacuum pump P1 may desirably be a diaphragm vacuum pump. The accumulator may desirably be a 300 cc volumetric vessel accumulator for example. Other volumetric vessel capacities are optionally utilized.

Pleural drainage systems may further provide for mobile suction by suction system 902. As described above, suction system 902 may provide suction independently, without attachment to an external suction source. Mobile suction by suction system 902 may be activated by way of a user-operated switch on control panel 906. As a mobile suction system, suction system 902 may provide −20 cmH$_2$O of suction, for example.

Pleural drainage systems in accordance with aspects of the present invention may further include an internal, rechargeable battery. In an exemplary embodiment, pleural drainage system 900 includes an internal lithium-ion battery (not shown). The internal battery may be recharged through a standard AC power connection. The internal battery may provide power for all of the electrical features of system 900, including but not limited to the vacuum suction indicator 912, the patient pressure indicator 916, the audible alarm, and the fluid-clearing device. The internal battery may further provide power to operate suction system 902 as a mobile suction system, as described above.

In order to optimize the functionality of a pleural drainage system such as systems 700, 800, or 900, the pleural drainage catheter system of the pleural drainage system is optionally provided with additional features.

Figure 21:
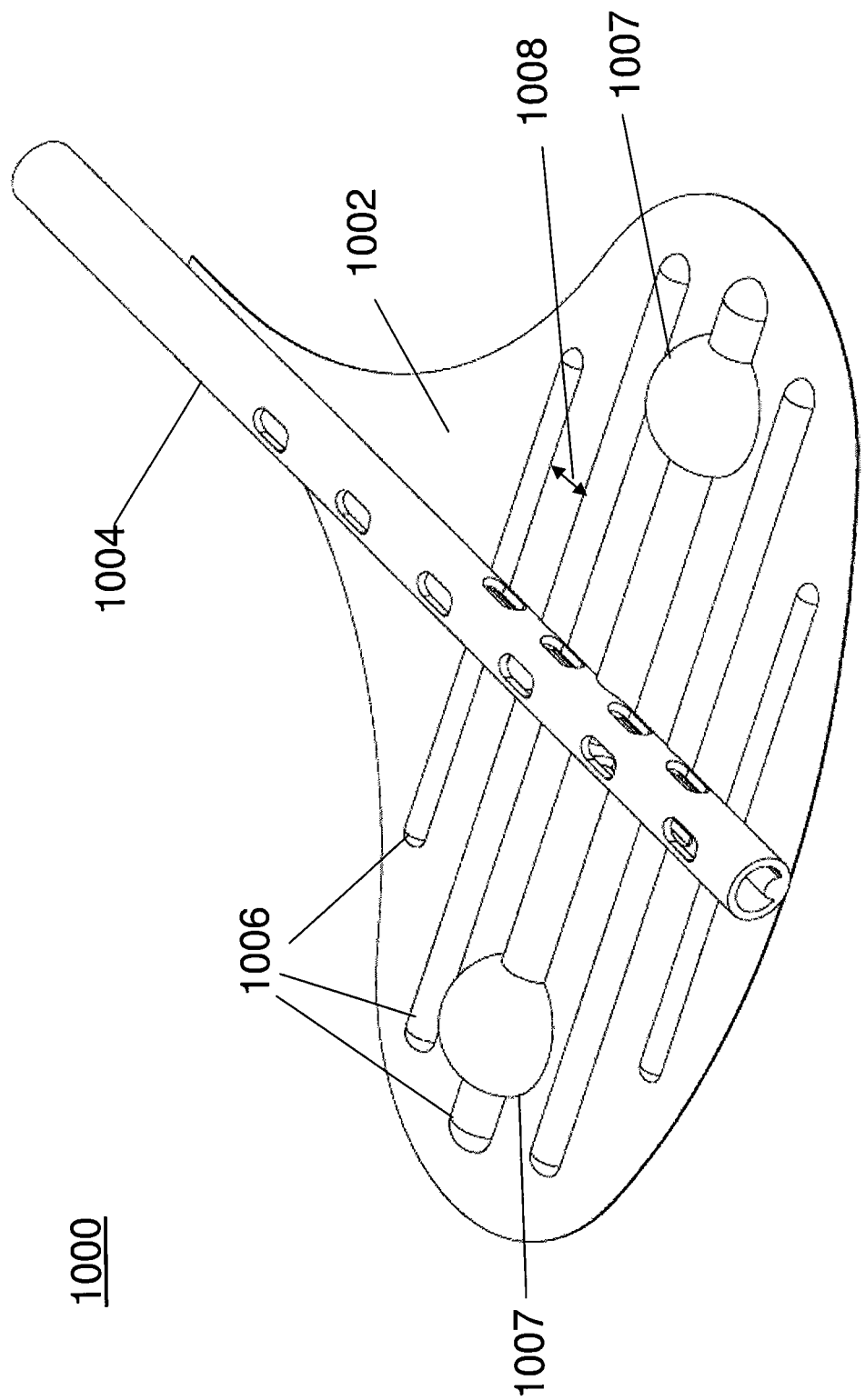
FIG. 21 is a top perspective view of another exemplary embodiment of a pleural drainage catheter system according to an aspect of the present invention.
Figure 22:
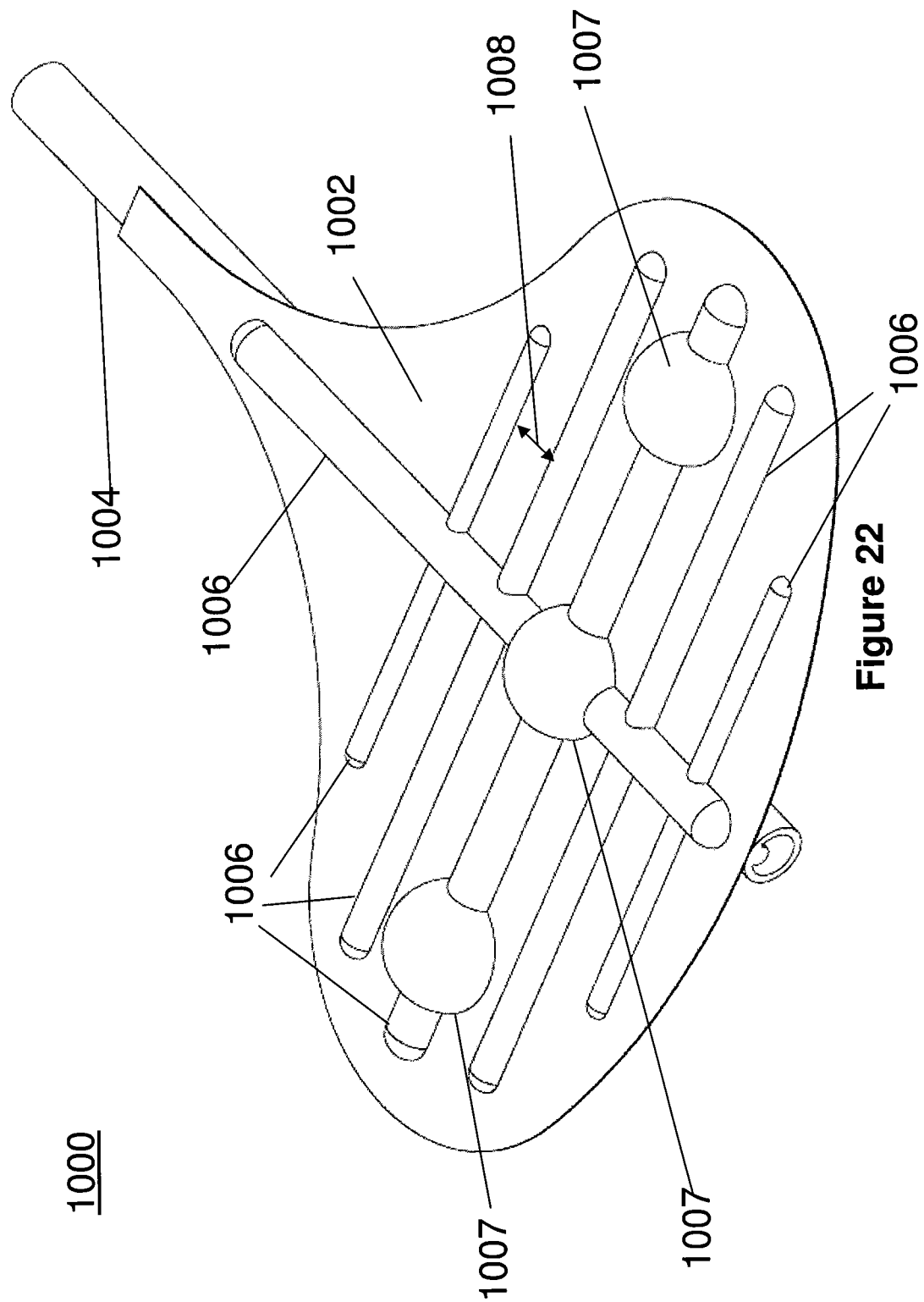
FIG. 22 is a bottom perspective view of the pleural drainage catheter system shown in FIGS. 21.
Figure 23:
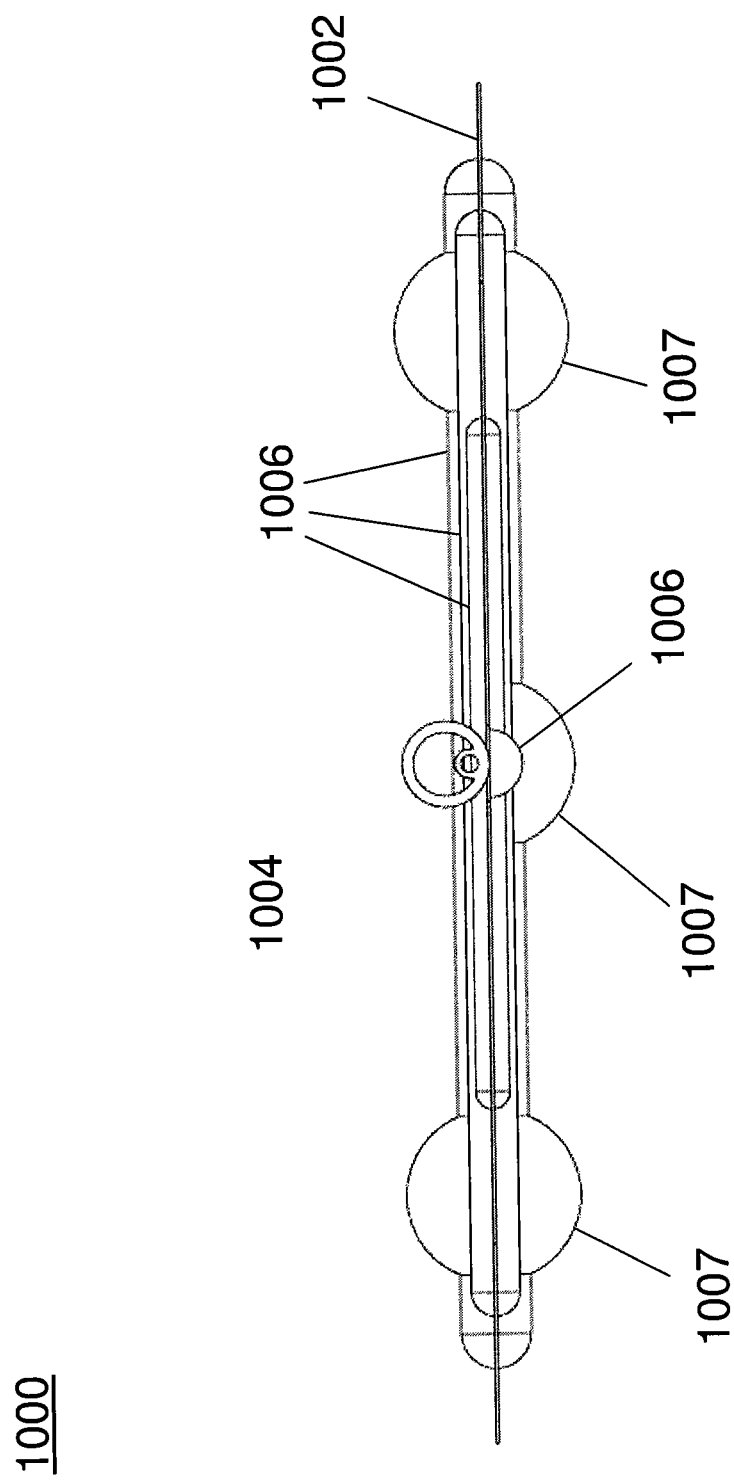
FIG. 23 is a cross-sectional end view of the pleural drainage catheter system shown in FIG. 21.

For example, FIGS. 21-23 depict another alternative exemplary embodiment of a pleural drainage catheter system 1000 in accordance with an aspect of the present invention. The pleural drainage catheter system 1000 is also configured to extend into a pleural cavity of a patient (not shown). The pleural drainage catheter system 1000 includes an inflatable membrane 1002 and a drainage catheter 1004 integrally coupled to inflatable membrane 1002. Pleural drainage catheter system 1000 is a pleural drainage catheter system substantially as described with respect to the above exemplary embodiments, except that it includes additional features as described below.

Inflatable membrane 1002 defines one or more tubelets 1006 when in an inflated state. While FIG. 21 illustrates five such tubelets 1006 extending outwardly from each side of drainage catheter 1004, it will be understood that fewer or more such tubelets can be provided. Tubelets 1006 may be formed by selectively sealing the two opposed layers of inflatable membrane 1002 to define the one or more tubelets 106.

The tubelets 1006 may be provided in the form of substantially straight structures, as illustrated, or in other curved or angled shapes to form inflatable ribs. While tubelets 1006 are illustrated as primarily cylindrical in shape, it will be understood that tubelets 1006 may have other shapes, as desired. Respective tubelets 1006 may have different lengths and/or cross-sectional areas, such that respective tubelets 1006 fill different volumes when inflatable membrane 1002 is inflated. As illustrated in FIGS. 21 and 22, it may be desirable that tubelets 1006 toward the center of inflatable membrane 1002 be larger than tubelets 1006 formed toward the periphery of inflatable membrane 1002. Additionally, one or more tubelets 1006 may be oriented to extend in other directions such as in a direction parallel to that of the drainage catheter 1004. As illustrated in FIGS. 22 and 23, a tubelet 1006 runs adjacent to drainage catheter 1004 and crosses other tubelets 1006. The tubelets 1006 that cross each other may, or may not, be in fluid flow communication with each other.

One or more tubelets 1006 may also include enlarged portions 1007. Enlarged portions 1007 have larger cross-sectional areas than tubelets 1006. One or more enlarged portions 1007 may be formed on at least one tubelet 1006. While enlarged portions 1007 are illustrated as primarily hemispherical in shape, it will be understood that enlarged portions 1007 may have other shapes or sizes, as desired. Respective enlarged portions 1007 may have different cross-sectional areas such that respective enlarged portions 1007 fill different volumes when inflatable membrane 1002 is inflated. As illustrated in FIGS. 21 and 23, it may be desirable that enlarged portions 1007 be formed on both sides of inflatable membrane 1002, and be formed in the center of inflatable membrane 1002.

Tubelets 1006 and enlarged portions 1007 define one or more passages 1008, as described above. The passages 1008 may function as drainage channels such that when inflatable membrane 1002 is in the inflated state, passages 1008 facilitate the movement of fluid along the external surface of inflatable membrane 1002 to drainage catheter 1004 for removal from the pleural cavity. Although not shown, drainage holes like holes 218 may be formed in the inflatable membrane 1002.

The catheter system 1000 also solves the problem of inadequate pleural drainage by providing multiple drainage channels during the continuous or selective inflation of the inflatable membrane 1002. Additionally, as described above, the inflation of inflatable membrane 1002 separates adjacent tissues limiting adhesion and fibrous formations. Specifically, forming tubelets 1006 having different shapes, sizes, and cross-sectional areas may advantageously further separate or dissect adjacent tissues and limit adhesion and fibrous formations, and enhance and facilitate better drainage of the pleural cavity. Further, enlarged portions 1007 may be positioned on inflatable membrane 1007 to provide pressure to specific areas of the pleural cavity, such as specific areas of loculations, thereby better separating tissue or providing an improved therapy. Enlarged portions 1007 may further be centrally located at the drainage catheter 1004 of system 1000, such as shown in FIG. 22, thereby facilitating inflation, deployment, retrieval, and retraction of system 1000. One or both of tubelets 1006 and enlarged portions 1007 can also be fabricated with a membrane material that permits the release of medicaments at controlled rates and pressures, as described above.

Systems and methods according to aspects of this invention can be used beneficially in the treatment of various physiological indications and conditions. For example, in the United States, approximately 1,200,000 patients develop pneumonia annually. Of these, approximately 40% develop Empyema. Further, approximately 5% of all pneumonia patients, or 60,000 patients, develop para-pneumonic effusion, and require an extended hospital stay and treatment.

The total charges for such treatment are well beyond the range of $60,000-$100,000 per patient. The length of a hospital stay for a patient with para-pneumonic effusion may range from 17-24 days for non-surgically treated patients and 9-13 days for surgically treated patients. Data indicates that hospitals such as Vanderbilt Medical Center, University of California Irvine Healthcare, and Emory's Crawford Long Hospital receive between 30-50 patients per year requiring treatment for advanced loculated Empyema.

Treatment for pleural empyema generally requires the removal of infected fluid from the pleural cavity of an affected patient. By utilizing systems and methods according to exemplary embodiments of this invention, suction can be applied to a larger region of the pleural cavity. Consequently, and often, fluid that is otherwise trapped in the pleural space can be removed by the suction catheter. Because parapneumonic effusions can become infected and progress to more chronic conditions and potentially death, the reduction of such effusions according to aspects of this invention can provide significant benefits. Additionally, systems and methods according to aspects of this invention can provide alternative ways to monitor an airleak. Such alternatives are believed to be especially beneficial in circumstances where significant clinical limitations to a patient may result from measuring low flows or by limiting the flow area through which the airflow must pass.

Disclosed embodiments of pleural drainage systems provide the clinical benefit of correlating measured pressures within the pleural space and within the inflatable membrane so as to selectively optimize the treatment regimen, such as by using a control algorithm, and therefore providing the preferred pulmonary therapy and healing response. Additionally, the benefit of a suction system according to exemplary embodiments that apply suction to a pleural drainage catheter combined with an inflatable membrane is the facilitation of pleural drainage and the associated reduction of potential infection caused by trapped fluid.

Another benefit of embodiments of the disclosed pleural drainage system is the means to measure the rate of pressure decay within the pleural space of the patient and correlate this measured response to an assessment of a patient airleak. This feature, whether used with or instead of direct measurements of an airleak, provides an alternative that allows the user to correlate the measured rate of pressure decay to an associated airleak without the need to restrict the flow or to incorporate an additional flow sensor.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A pleural drainage system configured to deliver a therapeutic treatment to the pleural cavity of a patient, said system comprising:

a pleural drainage catheter system including an inflatable membrane having a deflated state and an inflated state, the pleural drainage catheter system also including a drainage catheter coupled to the inflatable membrane, the drainage catheter defining a drainage lumen, a plurality of drainage openings through which fluid is drawn into the drainage lumen from the pleural cavity, and an inflation lumen coupled for flow of inflation fluid to and from an interior of the inflatable membrane, wherein the inflatable membrane extends both proximally and distally with respect to the plurality of drainage openings, and wherein the inflatable membrane comprises a surface extending away from the drainage catheter adjacent one or more of the plurality of drainage openings, and inflatable, portions proximal and distal to the surface, the inflatable portions extending outwardly from the surface when the inflatable membrane is in the inflated state;

a suction system coupled to the drainage catheter of the pleural drainage catheter system and connected to apply suction to the drainage lumen of the drainage catheter and to draw fluid into the drainage lumen of the drainage catheter through the drainage openings defined by the drainage catheter;

a fluid collector coupled to receive fluid from the drainage lumen of the drainage catheter; and an inflation system coupled to the drainage catheter of the pleural drainage catheter system and connected to apply pressure to the inflation lumen of the drainage catheter and to deliver inflation fluid to the interior of the inflatable membrane through the inflation lumen defined by the drainage catheter.

2. The pleural drainage system of claim 1, said suction system being configured to monitor the suction applied to the drainage lumen of the drainage catheter.

3. The pleural drainage system of claim 1, further comprising an electronic controller coupled to at least one of the suction system and the inflation system.

4. The pleural drainage system of claim 1, said inflation system comprising a pump configured for active inflation and active deflation of the inflatable membrane.

5. The pleural drainage system of claim 1, said inflation system comprising a sensor configured to sense the pressure of the inflation fluid.

6. The pleural drainage system of claim 1, said inflation system comprising a maximum pressure check valve configured to release inflation fluid from the pleural drainage system when a predetermined pressure is achieved.

7. The pleural drainage system of claim 1, further comprising a scanner for obtaining patient identification information.

8. The pleural drainage system of claim 1, further comprising a display including at least one of a user interface and system controls.

9. The pleural drainage system of claim 1, further comprising a memory for storing at least one of patient data and backup data.

10. The pleural drainage system of claim 1, the inflatable membrane comprising two opposed layers formed from a bio-compatible material, the layers being positioned substantially adjacent one another in the deflated state and at least portions of the respective layers being spaced from one another in the inflated state.

11. The pleural drainage system of claim 1, further comprising a connection for the transfer of data to and from the pleural drainage system.

12. The pleural drainage system of claim 1, further comprising an audible alarm.

13. The pleural drainage system of claim 1, said inflation system being configured to monitor the pressure of inflation fluid in the inflatable membrane and to measure the exerted pressure within the pleural cavity.

14. The pleural drainage system of claim 13, further comprising a pressure sensor module having a pressure sensor, a processor, and a sensor access probe.

15. The pleural drainage system of claim 1, wherein the inflatable portions of the inflatable membrane define tubelets when the inflatable membrane is in the inflated state, the tubelets positioned both proximally and distally with respect to one or more of the plurality of drainage openings.

\* \* \* \* \*